US011926841B2

(12) United States Patent
Koszinowski et al.

(10) Patent No.: US 11,926,841 B2
(45) Date of Patent: Mar. 12, 2024

(54) AAV-BASED CONDITIONAL EXPRESSION SYSTEM

(71) Applicant: SIRION BIOTECH GmbH, Planegg (DE)

(72) Inventors: Ulrich Koszinowski, Diessen am Ammersee (DE); Simona Langer, Munich (DE); Zsolt Ruzsics, Diessen am Ammersee (DE); Christian Thirion, Munich (DE)

(*) Notice: Subject to any disclaimer, the term of this patent is extended or adjusted under 35 U.S.C. 154(b) by 30 days.

(21) Appl. No.: 17/481,576

(22) Filed: Sep. 22, 2021

(65) Prior Publication Data
US 2022/0073947 A1  Mar. 10, 2022

Related U.S. Application Data

(63) Continuation of application No. 16/073,488, filed as application No. PCT/EP2017/051944 on Jan. 30, 2017, now Pat. No. 11,155,831.

(30) Foreign Application Priority Data

Jan. 29, 2016 (EP) .................................. 16153329

(51) Int. Cl.
| | |
|---|---|
| C07H 21/04 | (2006.01) |
| C12N 15/86 | (2006.01) |
| C12Q 1/02 | (2006.01) |
| C12Q 1/6897 | (2018.01) |
| C12Q 1/70 | (2006.01) |

(52) U.S. Cl.
CPC ............ *C12N 15/86* (2013.01); *C12Q 1/025* (2013.01); *C12Q 1/6897* (2013.01); *C12Q 1/70* (2013.01); *C12N 2750/14143* (2013.01); *C12N 2750/14152* (2013.01); *C12N 2830/002* (2013.01)

(58) Field of Classification Search
None
See application file for complete search history.

(56) References Cited

PUBLICATIONS

Office action and search report issued by the China National Intellectual Property Administration (CNIPA) in counterpart Chinese Application No. 201780021155.5 dated Nov. 16, 2021.
English translation of office action and search report issued by the China National Intellectual Property Administration (CNIPA) in counterpart Chinese Application No. 201780021155.5 dated Nov. 16, 2021.

(Continued)

*Primary Examiner* — M Franco G Salvoza
(74) *Attorney, Agent, or Firm* — Perdue IP Law, APC

(57) ABSTRACT

The present invention relates to a cell comprising (aa) a nucleic acid comprising in 5' to 3' direction (i) at least one adeno-associated virus (AAV) inverted terminal repeat (ITR) sequence; (ii) a promoter which is capable of being activated by (a) helper polypeptide(s) and optionally (a) helper polynucleotide(s); and (iii) a transgenic coding sequence under the control of said promoter of (aa)(ii); and (ab) a nucleic acid comprising in 5' to 3' direction (i) a promoter which is capable of being activated by said helper polypeptide(s) and optionally said helper polynucleotide(s); and (ii) at least one AAV rep gene coding sequence under the control of said promoter of (ab)(i); wherein said cell does not comprise an AAV cap gene and/or is not able to express any AAV cap gene product.

17 Claims, 14 Drawing Sheets

Specification includes a Sequence Listing.

(56) References Cited

PUBLICATIONS

Mietzsch, Mario et al. "OneBac: platform for scalable and high-titer production of adeno-associated virus serotype 1-12 vectors for gene therapy." Human gene therapy vol. 25,3 (2014): 212-22. doi:10.1089/hum.2013.184.

Examination Report issued by the Canadian Intellectual Property Office (CIPO) in counterpart Canadian Application No. 3,012,409 dated Nov. 23, 2023.

Moore A. et al., "Vaccinia virus as a subhelper for AAV replication and packaging", Mol. Ther. Methods Clin. Dev., 2, Article 15044, published online Nov. 18, 2015 (Nov. 18, 2015) DOI: 10.1038/mtm.2015.44.

```
LOCUS       pAV1-GLuc-Hyg_PA          8977 bp    DNA     circular UNA 01-SEP-
2015  (SEQ ID NO: 1)
DEFINITION  .
ACCESSION   urn.local...1440430013470.14
VERSION     urn.local...1440430013470.14
KEYWORDS    .
SOURCE
  ORGANISM  .
            .
FEATURES             Location/Qualifiers
     repeat_region   1..145
                     /label="ITR5"
     misc_feature    190..310
                     /note="promoter eukaryotic"
                     /label="P5"
     misc_feature    255..261
                     /label="P5-TATAbox"
     CDS             321..2186
                     /label="rep"
     misc_feature    720..899
                     /note="promoter eukaryotic"
                     /label="P19"
     misc_feature    843..849
                     /label="P19-TATAbox"
     CDS             993..2186
                     /label="rep"
     misc_feature    1700..1879
                     /note="promoter eukaryotic"
                     /label="P40"
     misc_feature    1823..1827
                     /label="P40-TATAbox"
     intron          1907..2227
                     /label="Intron_cap"
     CDS             2287..2844
                     /product="Gaussia luciferase"
                     /gene="GLuc"
                     /label="GLuc"
     misc_feature    2853..3120
                     /note="promoter eukaryotic"
                     /label="PSV40e"
     CDS             3177..4202
                     /label="Hyg"
     repeat_region   complement(4726..4854)
                     /label="ITR3"
     CDS             5140..6003
                     /label="AP(R)"
     rep_origin      6761
                     /label="ORI"
     CDS             complement(7190..7381)
                     /label="ROP"
```

FIG. 1C

ORIGIN
```
   1 tgggccactc cctctctgcg cgctcgctcg ctcactgagg ccggcgacc  aaaggtcgcc
  61 cgacgcccgg gctttgcccg ggcggcctca gtgagcgagc gagcgcgcag agagggagtg
 121 gccaactcca tcactagggg ttcctggagg ggtggagtcg tgacgtgaat tacgtcatag
 181 ggttagggag gtcctgtatt agaggtcacg tgagtgtttt gcgacatttt gcgacaccat
 241 gtggtcacgc tgggtattta agcccgagtg agcacgcagg gtctccattt tgaagcggga
 301 ggtttgaacg cgcagccgcc atgccgggt  tttacgagat tgtgattaag gtccccagcg
 361 accttgacgg gcatctgccc ggcatttctg acagctttgt gaactgggtg ccgagaagg
 421 aatgggagtt gccgccagat tctgacatgg atctgaatct gattgagcag gcaccctga
 481 ccgtggccga gaagctgcag cgcgactttc tgacggaatg gcgccgtgtg agtaaggccc
 541 cggaggccct tttctttgtg caatttgaga agggagagag ctacttccac atgcacgtgc
 601 tcgtggaaac caccggggtg aaatccatgg ttttgggacg tttcctgagt cagattcgcg
 661 aaaaactgat tcagagaatt taccgcggga tcgagccgac tttgccaaac tggttcgcgg
 721 tcacaaagac cagaaatggc gccggaggcg gaacaaggt ggtggatgag tgctacatcc
 781 ccaattactt gctccccaaa acccagcctg agctccagtg ggcgtggact aatatggaac
 841 agtatttaag cgcctgtttg aatctcacgg agcgtaaacg gttggtggcg cagcatctga
 901 cgcacgtgtc gcagacgcag gagcagaaca aagagaatca gaatcccaat tctgatgcgc
 961 cggtgatcag atcaaaaact tcagccaggt acatggagct ggtcgggtgg ctcgtggaca
1021 agggattac ctcggagaag cagtggatcc aggaggacca ggcctcatac atctccttca
1081 atgcggcctc caactcgcgg tcccaaatca aggctgcctt ggacaatgcg ggaaagatta
1141 tgagcctgac taaaaccgcc cccgactacc tggtgggcca gcagcccgtg gaggacattt
1201 ccagcaatcg gatttataaa attttggaac taaacgggta cgatccccaa tatgcggctt
1261 ccgtctttct gggatgggcc acgaaaaagt tcggcaagag gaacaccatc tggctgtttg
1321 ggcctgcaac taccgggaag accaacatcg cggaggccat agcccacact gtgcccttct
1381 acggtgcgt  aaactggacc aatgagaact ttccccttcaa cgactgtgtc gacaagatgg
1441 tgatctggtg ggaggagggg aagatgaccg ccaaggtcgt ggagtcggcc aaagccattc
1501 tcggaggaag caaggtgcgc gtggaccaga aatgcaagtc ctcggcccag atagacccga
1561 ctcccgtgat cgtcacctcc aacaccaaca tgtgcgccgt gattgacggg aactcaacga
1621 ccttcgaaca ccagcagccg ttgcaagacc ggatgttcaa atttgaactc accgccgtc
1681 tggatcatga ctttgggaag gtcaccaagc aggaagtcaa agacttttc  cggtgggcaa
1741 aggatcacgt ggttgaggtg gagcatgaat tctacgtcaa aaagggtgga gccaagaaaa
1801 gacccgcccc cagtgacgca gatataagtg agcccaaacg ggtgcgcgag tcagttgcgc
1861 agccatcgac gtcagacgcg gaagcttcga tcaactacgc agacaggtac aaaacaaat
1921 gttctcgtca cgtgggcatg aatctgatgc tgtttccctg cagacaatgc gagagaatga
1981 atcagaattc aaatatctgc ttcactcacg gacagaaaga ctgtttagag tgctttcccg
2041 tgtcagaatc tcaacccgtt tctgtcgtca aaaaggcgta tcagaaactg tgctacattc
2101 atcatatcat gggaaaggtg ccagacgctt gcactgcctg cgatctggtc aatgtggatt
2161 tggatgactg catctttgaa caataaatga tttaaatcag gtatggctgc cgatggttat
2221 cttccagatt ggctcgagga cactctctct gagctagctt cgtacggatc ctcggatcca
2281 gccaccatgg gagtcaaagt tctgtttgcc ctgatctgca tcgctgtggc cgaggccaag
2341 cccaccgaga caacgaaga  cttcaacatc gtggccgtgg ccagcaactt cgcgaccacg
2401 gatctcgatg ctgaccgcgg gaagttgccc ggcaagaagc tgccgctgga ggtgctcaaa
2461 gagatggaag ccaatgcccg gaaagctggc tgcaccaggg gtgtctgat  ctgcctgtcc
2521 cacatcaagt gcacgcccaa gatgaagaag ttcatcccag gacgctgcca cacctacgaa
2581 ggcgacaaag agtccgcaca gggcggcata ggcgaggcga tgtcgacat  tcctgagatt
2641 cctgggttca aggacttgga gcccatggag cagttcatcg cacaggtcga tctgtgtgtg
2701 gactgcacaa ctggctgcct caagggcttg gccaacgtgc agtgttctga cctgctcaag
2761 aagtggctgc cgcaacgctg tgcgaccttt gccagcaaga tccagggcca ggtggacaag
2821 atcaagggg  ccggtggtga ctaagcggcc gcgtgtggaa agtccccagg ctccccagca
2881 ggcagaagta tgcaaagcat gcatctcaat tagtcagcaa ccaggtgtgg aaagtcccca
2941 ggctccccag caggcagaag tatgcaaagc atgcatctca attagtcagc aaccatagtc
3001 ccgcccctaa ctccgcccat cccgcccta  actccgccca gttccgccca ttctccgccc
3061 catggctgac taatttttt  tatttatgca gaggccgagg ccgcctcggc ctctgagcta
3121 ttccagaagt agtgaggagg cttttttgga ggcctaggct tttgcaaaaa gcttccatga
3181 aaagcctga  actcaccgcg acgtctgtcg agaagtttct gatcgaaaag ttcgacagcg
3241 tctccgacct gatgcagctc tcggagggcg aagaatctcg tgctttcagc ttcgatgtag
3301 gagggcgtgg atatgtcctg cggtaaata  gctgcgccga tggtttctac aaagatcgtt
3361 atgtttatcg gcactttgca tcggccgcgc tcccgattcc ggaagtgctt gacattgggg
```

FIG. 1C continued

```
3421 aattcagcga gagcctgacc tattgcatct cccgccgtgc acagggtgtc acgttgcaag
3481 acctgcctga aaccgaactg cccgctgttc tgcagccggt cgcggaggcc atggatgcga
3541 tcgctgcggc cgatcttagc cagacgagcg ggttcggccc attcggaccg caaggaatcg
3601 gtcaatacac tacatggcgt gatttcatat gcgcgattgc tgatccccat gtgtatcact
3661 ggcaaactgt gatggacgac accgtcagtg cgtccgtcgc gcaggctctc gatgagctga
3721 tgcttttgggc cgaggactgc cccgaagtcc ggcacctcgt gcacgcggat ttcggctcca
3781 acaatgtcct gacggacaat ggccgcataa cagcggtcat tgactggagc gaggcgatgt
3841 tcggggattc ccaatacgag gtcgccaaca tcttcttctg gaggccgtgg ttggcttgta
3901 tggagcagca gacgcgctac ttcgagcgga ggcatccgga gcttgcagga tcgccgcggc
3961 tccggcgta tatgctccgc attggtcttg accaactcta tcagagcttg gttgacggca
4021 atttcgatga tgcagcttgg gcgcagggtc gatgcgacgc aatcgtccga tccggagccg
4081 ggactgtcgg gcgtacacaa atcgcccgca gaagcgcggc cgtctggacc gatggctgtg
4141 tagaagtact cgccgatagt ggaaaccgac gccccagcac tcgtccgagg caaaggaat
4201 agagttctag aggatcataa tcagccatac cacagggccc atctgggcaa agattccaca
4261 cacggacgga cattttcacc cctctcccct catgggtgga ttcggactta acaccctcc
4321 tccacagatt ctcatcaaga acaccccggt acctgcgaat ccttcgacca ccttcagtgc
4381 ggcaaagttt gcttccttca tcacacagta ctccacggga cacggtcagc gtggagatcg
4441 agtgggagct gcagaaggaa aacagcaaac gctggaatcc cgaaattcag tacacttcca
4501 actacaacaa gtctgttaat cgtggactta ccgtggatac taatggcgtg tattcagagc
4561 ctcgccccat tggcaccaga tacctgactc gtaatctgta attgcttgtt aatcaataaa
4621 ccgtttaatt cgtttcagtt gaactttggt ctctgcgtat ttctttctta tctagtttcc
4681 atggctacgt agataagtag catggcgggt taatcattaa ctacaaggaa ccctagtga
4741 tggagttggc cactccctct ctgcgcgctc gctcgctcac tgaggccggg cgaccaaagg
4801 tcgccgacg cccggcttt gccgggcgg cctcagtgag cgagcgagcg cgcagagagg
4861 gacagatctt ccatacctac cagttctgcg cctgcagcaa tggcaacaac gttgcccgga
4921 tccggtcgcg cgaattcttg aagacgaaag ggcctcgtga tacgcctatt tttataggtt
4981 aatgtcatga taataatggt ttcttagacg tcaggtgca cttttcgggg aaatgtgcgc
5041 ggaacccta tttgtttatt tttctaaata cattcaaata tgtatccgct catgagacaa
5101 taaccctgat aaatgcttca ataatattga aaaggaaga gtatgagtat tcaacatttc
5161 cgtgtcgccc ttattccctt tttgcggca ttttgccttc ctgttttgc tcacccagaa
5221 acgctggtga agtaaaaga tgctgaagat cagttgggtg cacgagtggg ttacatcgaa
5281 ctggatctca acagcggtaa gatccttgag agttttcgcc ccgaagaacg ttttccaatg
5341 atgagcactt ttaaagttct gctatgtggc gcggtattat cccgtgttga cgccgggcaa
5401 gagcaactcg gtcgccgcat acactattct cagaatgact tggttgagta ctcaccagtc
5461 acagaaaagc atcttacgga tggcatgaca gtaagagaat tatgcagtgc tgccataacc
5521 atgagtgata acactgcggc caacttactt ctgacaacga tcggaggacc gaaggagcta
5581 accgcttttt tgcacaacat ggggatcat gtaactcgcc ttgatcgttg gaaccggag
5641 ctgaatgaag ccataccaaa cgacgagcgt gacaccacga tgcctgcagc aatggcaaca
5701 acgttgcgca aactattaac tggcgaacta cttactctag cttcccggca acaattaata
5761 gactggatgg aggcggataa agttgcagga ccacttctgc gctcggccct tccggctggc
5821 tggtttattg ctgataaatc tggagccggt gagcgtgggt ctcgcggtat cattgcagca
5881 ctggggccag atggtaagcc ctcccgtatc gtagttatct acacgacggg gagtcaggca
5941 actatggatg aacgaaatag acagatcgct gagataggtg cctcactgat taagcattgg
6001 taactgtcag accaagttta ctcatatata ctttagattg atttaaaact tcatttttaa
6061 tttaaaagga tctaggtgaa gatcctttt gataatctca tgaccaaaat cccttaacgt
6121 gagttttcgt tccactgagc gtcagacccc gtagaaaaga tcaaaggatc ttcttgagat
6181 cctttttttc tgcgcgtaat ctgctgcttg caaacaaaaa accaccgct accagcggtg
6241 gtttgtttgc cggatcaaga gctaccaact cttttccga aggtaactgg cttcagcaga
6301 gcgcagatac caaatactgt ccttctagtg tagccgtagt taggccacca cttcaagaac
6361 tctgtagcac cgcctacata cctcgctctg ctaatcctgt taccagtggc tgctgccagt
6421 ggcgataagt cgtgtcttac cgggttggac tcaagacgat agttaccgga taaggcgcag
6481 cggtcgggct gaacggggg ttcgtgcaca cagcccagct tggagcgaac gacctacacc
6541 gaactggagat acctacagcg tgagctatga gaaagcgcca cgcttcccga agggagaaag
6601 gcggacaggt atccggtaag cggcagggtc ggaacaggag agcgcacgag ggagcttcca
6661 gggggaaacg cctggtatct ttatagtcct gtcgggtttc gccacctctg acttgagcgt
6721 cgatttttgt gatgctcgtc aggggggcgg agcctatgga aaaacgccag caacgcggcc
6781 tttttacggt tcctggcctt ttgctggcct tttgctcaca tgttctttcc tgcgttatcc
```

FIG. 1C continued

```
6841 cctgattctg tggataaccg tattaccgcc tttgagtgag ctgataccgc tcgccgcagc
6901 cgaacgaccg agcgcagcga gtcagtgagc gaggaagcgg aagagcgcct gatgcggtat
6961 tttctcctta cgcatctgtg cggtatttca caccgcatat ggtgcactct cagtacaatc
7021 tgctctgatg ccgcatagtt aagccagtat acactccgct atcgctacgt gactgggtca
7081 tggctgcgcc ccgacacccg ccaacacccg ctgacgcgcc ctgacgggct tgtctgctcc
7141 cggcatccgc ttacagacaa gctgtgaccg tctccgggag ctgcatgtgt cagaggtttt
7201 caccgtcatc accgaaacgc gcgaggcagc tgcggtaaag ctcatcagcg tggtcgtgaa
7261 gcgattcaca gatgtctgcc tgttcatccg cgtccagctc gttgagtttc tccagaagcg
7321 ttaatgtctg gcttctgata agcgggcca tgttaagggc ggttttttcc tgtttggtca
7381 ctgatgcctc cgtgtaaggg ggatttctgt tcatgggggt aatgataccg atgaaacgag
7441 agaggatgct cacgatacgg ttactgatg atgaacatgc ccggttactg aacgttgtg
7501 agggtaaaca actggcggta tggatgcggc gggaccagag aaaaatcact cagggtcaat
7561 gccagcgctt cgttaataca gatgtaggtg ttccacaggg tagccagcag catcctgcga
7621 tgcagatccg gaacataatg gtgcagggcg ctgacttccg cgtttccaga ctttacgaaa
7681 cacggaaacc gaagaccatt catgttgttg ctcaggtcgc agacgttttg cagcagcagt
7741 cgcttcacgt tcgctcgcgt atcggtgatt cattctgcta accagtaagg caaccccgcc
7801 agcctagccg ggtcctcaac gacaggagca cgatcatgcg cacccgtggc caggacccaa
7861 cgctgcccga gatgcgccgc gtgcggctgc tggagatggc ggacgcgatg gatatgttct
7921 gccaagggtt ggtttgcgca ttcacagttc tccgcaagaa ttgattggct ccaattcttg
7981 gagtggtgaa tccgttagcg aggtgccgcc ggcttccatt caggtcgagg tggcccggct
8041 ccatgcaccg cgacgcaacg cggggaggca gacaaggtat agggcggcgc ctacaatcca
8101 tgccaacccg ttccatgtgc tcgccgaggc ggcataaatc gccgtgacga tcagcggtcc
8161 agtgatcgaa gttaggctgg taagagccgc gagcgatcct tgaagctgtc cctgatggtc
8221 gtcatctacc tgcctggaca gcatgcctg caacgcgggc atcccgatgc cgccggaagc
8281 gagaagaatc ataatgggga aggccatcca gcctcgcgtc gcgaacgcca gcaagacgta
8341 gcccagcgcg tcggccgcca tgccggcgat aatggcctgc ttctcgccga aacgtttggt
8401 ggcgggacca gtgacgaagg cttgagcgag ggcgtgcaag attccgaata ccgcaagcga
8461 caggccgatc atcgtcgcgc tccagcgaaa gcggtcctcg ccgaaaatga cccagagcgc
8521 tgccggcacc tgtcctacga gttgcatgat aaagaagaca gtcataagtg cggcgacgat
8581 agtcatgccc cgcgcccacc ggaaggagct gactgggttg aaggctctca agggcatcgg
8641 tcgacgctct cccttatgcg actcctgcat taggaagcag cccagtagta ggttgaggcc
8701 gttgagcacc gccgccgcaa ggaatggtgc atgcaaggag atggcgccca cagtccccc
8761 ggccacgggg cctgccacca tacccacgcc gaaacaagcg ctcatgagcc cgaagtggcg
8821 agccgatct tcccatcgg tgatgtcggc gatataggcg ccagcaaccg cacctgtggc
8881 gccggtgatg ccggccacga tgcgtccggc gtagagctct agagctctag agaattctca
8941 tgtttgacag cttatcatcg ataagcttct agagatc
```

FIG. 1C continued

Rep 68 protein (SEQ ID NO: 6)
MPGFYEIVIKVPSDLDEHLPGISDSFVNWVAEKEWELPPDSDMDLNLIEQAPLTVAEKLQRDFLTEWRRVSKAPEA
LFFVQFEKGESYFHMHVLVETTGVKSMVLGRFLSQIREKLIQRIYRGIEPTLPNWFAVTKTRNGAGGGNKVVDECY
IPNYLLPKTQPELQWAWTNMEQYLSACLNLTERKRLVAQHLTHVSQTQEQNKENQNPNSDAPVIRSKTSARYMELV
GWLVDKGITSEKQWIQEDQASYISFNAASNSRSQIKAALDNAGKIMSLTKTAPDYLVGQQPVEDISSNRIYKILEL
NGYDPQYAASVFLGWATKKFGKRNTIWLFGPATTGKTNIAEAIAHTVPFYGCVNWTNENFPFNDCVDKMVIWWEEG
KMTAKVVESAKAILGGSKVRVDQKCKSSAQIDPTPVIVTSNTNMCAVIDGNSTTFEHQQPLQDRMFKFELTRRLDH
DFGKVTKQEVKDFFRWAKDHVVEVEHEFYVKKGGAKKRPAPSDADISEPKRVRESVAQPSTSDAEASINYADRLAR
GHSL Rep 78 protein (SEQ ID NO: 7)
MPGFYEIVIKVPSDLDEHLPGISDSFVNWVAEKEWELPPDSDMDLNLIEQAPLTVAEKLQRDFLTEWRRVSKAPEA
LFFVQFEKGESYFHMHVLVETTGVKSMVLGRFLSQIREKLIQRIYRGIEPTLPNWFAVTKTRNGAGGGNKVVDECY
IPNYLLPKTQPELQWAWTNMEQYLSACLNLTERKRLVAQHLTHVSQTQEQNKENQNPNSDAPVIRSKTSARYMELV
GWLVDKGITSEKQWIQEDQASYISFNAASNSRSQIKAALDNAGKIMSLTKTAPDYLVGQQPVEDISSNRIYKILEL
NGYDPQYAASVFLGWATKKFGKRNTIWLFGPATTGKTNIAEAIAHTVPFYGCVNWTNENFPFNDCVDKMVIWWEEG
KMTAKVVESAKAILGGSKVRVDQKCKSSAQIDPTPVIVTSNTNMCAVIDGNSTTFEHQQPLQDRMFKFELTRRLDH
DFGKVTKQEVKDFFRWAKDHVVEVEHEFYVKKGGAKKRPAPSDADISEPKRVRESVAQPSTSDAEASINYADRYQN
KCSRHVGMNLMLFPCRQCERMNQNSNICFTHGQKDCLECFPVSESQPVSVVKKAYQKLCYIHHIMGKVPDACTACD
LVNVDLDDCIFEQ Rep 40 protein (SEQ ID NO: 8)
MELVGWLVDKGITSEKQWIQEDQASYISFNAASNSRSQIKAALDNAGKIMSLTKTAPDYLVGQQPVEDISSNRIYK
ILELNGYDPQYAASVFLGWATKKFGKRNTIWLFGPATTGKTNIAEAIAHTVPFYGCVNWTNENFPFNDCVDKMVIW
WEEGKMTAKVVESAKAILGGSKVRVDQKCKSSAQIDPTPVIVTSNTNMCAVIDGNSTTFEHQQPLQDRMFKFELTR
RLDHDFGKVTKQEVKDFFRWAKDHVVEVEHEFYVKKGGAKKRPAPSDADISEPKRVRESVAQPSTSDAEASINYAD
RLARGHSL Rep 52 protein (SEQ ID NO: 9)
MELVGWLVDKGITSEKQWIQEDQASYISFNAASNSRSQIKAALDNAGKIMSLTKTAPDYLVGQQPVEDISSNRIYK
ILELNGYDPQYAASVFLGWATKKFGKRNTIWLFGPATTGKTNIAEAIAHTVPFYGCVNWTNENFPFNDCVDKMVIW
WEEGKMTAKVVESAKAILGGSKVRVDQKCKSSAQIDPTPVIVTSNTNMCAVIDGNSTTFEHQQPLQDRMFKFELTR
RLDHDFGKVTKQEVKDFFRWAKDHVVEVEHEFYVKKGGAKKRPAPSDADISEPKRVRESVAQPSTSDAEASINYAD
RYQNKCSRHVGMNLMLFPCRQCERMNQNSNICFTHGQKDCLECFPVSESQPVSVVKKAYQKLCYIHHIMGKVPDAC
TACDLVNVDLDDCIFEQ

FIG. 1D

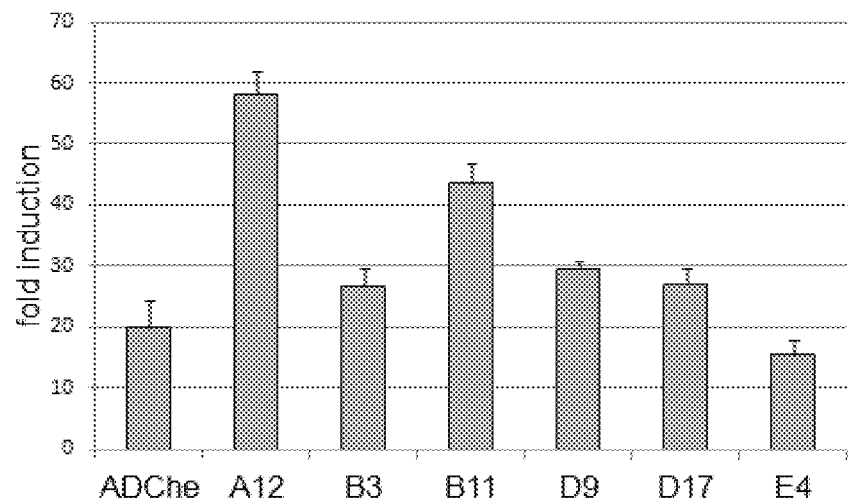
FIG. 7
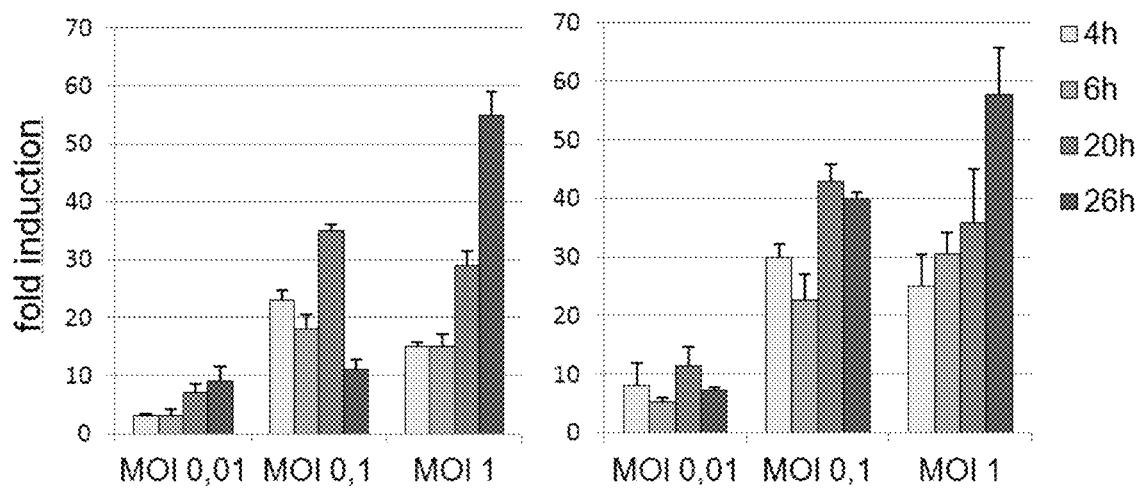
FIG. 8A  FIG. 8B

SEQUENCE LISTING

<160> NUMBER OF SEQ ID NOS: 10

<210> SEQ ID NO 1
<211> LENGTH: 8977
<212> TYPE: DNA
<213> ORGANISM: Artificial Sequence
<220> FEATURE:
<223> OTHER INFORMATION: Conditional expression system

<400> SEQUENCE: 1

```
atcgataagc ttctagagat ctgggccact ccctctctgc gcgctcgctc gctcactgag      60
gccgggcgac caaaggtcgc ccgacgcccg ggctttgccc gggcggcctc agtgagcgag     120
cgagcgcgca gagagggagt ggccaactcc atcactaggg gttcctggag gggtggagtc     180
gtgacgtgaa ttacgtcata gggttaggga ggtcctgtat tagaggtcac gtgagtgttt     240
tgcgacattt tgcgacacca tgtggtcacg ctgggtattt aagcccgagt gagcacgcag     300
ggtctccatt ttgaagcggg aggtttgaac gcgcagccgc catgccgggg ttttacgaga     360
ttgtgattaa ggtccccagc gaccttgacg ggcatctgcc cggcatttct gacagctttg     420
tgaactgggt ggccgagaag gaatgggagt tgccgccaga ttctgacatg gatctgaatc     480
tgattgagca ggcaccctg accgtggccg agaagctgca gcgcgacttt ctgacggaat      540
ggcgccgtgt gagtaaggcc ccggaggccc ttttctttgt gcaatttgag aagggagaga     600
gctacttcca catgcacgtg ctcgtggaaa ccacgggt gaaatccatg gttttgggac        660
gtttcctgag tcagattcgc gaaaaactga ttcagagaat ttaccgcggg atcgagccga     720
ctttgccaaa ctggttcgcg gtcacaaaga ccagaaatgg cgccggaggc gggaacaagg     780
tggtggatga gtgctacatc cccaattact tgctccccaa aacccagcct gagctccagt     840
gggcgtggac taatatggaa cagtatttaa gcgcctgttt gaatctcacg gagcgtaaac     900
ggttggtggc gcagcatctg acgcacgtgt cgcagacgca ggagcagaac aaagagaatc     960
agaatcccaa ttctgatgcg ccggtgatca gatcaaaaac ttcagccagg tacatggagc    1020
tggtcgggtg gctcgtggac aagggattc cctcggagaa gcagtggatc caggaggacc     1080
aggcctcata catctccttc aatgcggcct ccaactcgcg gtcccaaatc aaggctgcct    1140
tggacaatgc gggaaagatt atgagcctga ctaaaaccgc ccccgactac ctggtgggcc    1200
agcagcccgt ggaggacatt tccagcaatc ggatttataa aattttggaa ctaaacgggt    1260
acgatcccca atatgcggct tccgtctttc tgggatgggc cacgaaaaag ttcggcaaga    1320
ggaacaccat ctggctgttt gggcctgcaa ctaccgggaa gaccaacatc gcggaggcca    1380
tagcccacac tgtgcccttc tacgggtgcg taaactggac caatgagaac tttccccttca   1440 acgactgtgt cgacaagatg gtgatctggt gggaggaggg gaagatgacc gccaaggtcg    1500
tggagtcggc caaagccatt ctcggaggaa gcaaggtgcg cgtggaccag aaatgcaagt    1560
cctcggccca gatagacccg actcccgtga tcgtcacctc caacaccaac atgtgcgccg    1620
tgattgacgg gaactcaacg accttcgaac accagcagcc gttgcaagac cggatgttca    1680
```

```
aatttgaact cacccgccgt ctggatcatg actttgggaa ggtcaccaag caggaagtca    1740
aagactttt  ccggtgggca aaggatcacg tggttgaggt ggagcatgaa ttctacgtca    1800
aaaagggtgg agccaagaaa agacccgccc ccagtgacgc agatataagt gagcccaaac    1860
gggtgcgcga gtcagttgcg cagccatcga cgtcagacgc ggaagcttcg atcaactacg    1920
cagacaggta ccaaaacaaa tgttctcgtc acgtgggcat gaatctgatg ctgtttccct    1980
gcagacaatg cgagagaatg aatcagaatt caaatatctg cttcactcac ggacagaaag    2040
actgttttaga gtgctttccc gtgtcagaat ctcaacccgt ttctgtcgtc aaaaaggcgt   2100
atcagaaact gtgctacatt catcatatca tgggaaaggt gccagacgct tgcactgcct    2160
gcgatctggt caatgtggat ttggatgact gcatctttga acaataaatg atttaaatca    2220
ggtatggctg ccgatggtta tcttccagat tggctcgagg acactctctc tgagctagct    2280
tcgtacggat cctcggatcc agccaccatg ggagtcaaag ttctgtttgc cctgatctgc    2340
atcgctgtgg ccgaggccaa gcccaccgag aacaacgaag acttcaacat cgtggccgtg    2400
gccagcaact tcgcgaccac ggatctcgat gctgaccgcg gaagttgcc  cggcaagaag    2460
ctgccgctgg aggtgctcaa agagatggaa gccaatgccc ggaaagctgg ctgcaccagg    2520
ggctgtctga tctgcctgtc ccacatcaag tgcacgccca agatgaagaa gttcatccca    2580
ggacgctgcc acacctacga aggcgacaaa gagtccgcac agggcggcat aggcgaggcg    2640
atcgtcgaca ttcctgagat tcctgggttc aaggacttgg agcccatgga gcagttcatc    2700
gcacaggtcg atctgtgtgt ggactgcaca actggctgcc tcaaagggct tgccaacgtg    2760
cagtgttctg acctgctcaa gaagtggctg ccgcaacgct gtgcgacctt tgccagcaag    2820
atccagggcc aggtggacaa gatcaagggg gccggtggtg actaagcggc cgcgtgtgga    2880
aagtccccag gctccccagc aggcagaagt atgcaaagca tgcatctcaa ttagtcagca    2940
accaggtgtg gaaagtcccc aggctcccca gcaggcagaa gtatgcaaag catgcatctc    3000
aattagtcag caaccatagt cccgccccta actccgccca tcccgcccct aactccgccc    3060
agttccgccc attctccgcc ccatggctga ctaatttttt ttatttatgc agaggccgag    3120
gccgcctcgg cctctgagct attccagaag tagtgaggag gctttttttgg aggcctaggc   3180
ttttgcaaaa agcttccatg aaaaagcctg aactcaccgc gacgtctgtc gagaagtttc    3240
tgatcgaaaa gttcgacagc gtctccgacc tgatgcagct ctcggagggc gaagaatctc    3300
gtgctttcag cttcgatgta ggagggcgtg gatatgtcct gcgggtaaat agctgcgccg    3360
atggtttcta caaagatcgt tatgtttatc ggcactttgc atcggccgcg ctcccgattc    3420
cggaagtgct tgacattggg gaattcagcg agagcctgac ctattgcatc tcccgccgtg    3480
cacagggtgt cacgttgcaa gacctgcctg aaaccgaact gcccgctgtt ctgcagccgg    3540
tcgcggaggc catggatgcg atcgctgcgg ccgatcttag ccagacgagc gggttcggcc    3600
cattcggacc gcaaggaatc ggtcaataca ctacatggcg tgatttcata tgcgcgattg    3660
ctgatcccca tgtgtatcac tggcaaactg tgatggacga caccgtcagt gcgtccgtcg    3720
cgcaggctct cgatgagctg atgctttggg ccgaggactg ccccgaagtc cggcacctcg    3780
tgcacgcgga tttcggctcc aacaatgtcc tgacggacaa tggccgcata acagcggtca   3840
ttgactggag cgaggcgatg ttcggggatt cccaatacga ggtcgccaac atcttcttct    3900
ggaggccgtg gttggcttgt atggagcagc agacgcgcta cttcgagcgg aggcatccgg    3960
agcttgcagg atcgccgcgg ctccgggcgt atatgctccg cattggtctt gaccaactct    4020
atcagagctt ggttgacggc aatttcgatg atgcagcttg ggcgcagggt cgatgcgacg    4080
```

```
caatcgtccg atccggagcc gggactgtcg ggcgtacaca aatcgcccgc agaagcgcgg    4140
ccgtctggac cgatggctgt gtagaagtac tcgccgatag tggaaaccga cgccccagca    4200
ctcgtccgag ggcaaaggaa tagagttcta gaggatcata atcagccata ccacagggcc    4260
catctgggca aagattccac acacggacgg acattttcac ccctctcccc tcatgggtgg    4320
attcggactt aaacaccctc ctccacagat tctcatcaag aacaccccgg tacctgcgaa    4380
tccttcgacc accttcagtg cggcaaagtt tgcttccttc atcacacagt actccacggg    4440
acacggtcag cgtggagatc gagtgggagc tgcagaagga aaacagcaaa cgctggaatc    4500
ccgaaattca gtacacttcc aactacaaca agtctgttaa tcgtggactt accgtggata    4560
ctaatggcgt gtattcagag cctcgcccca ttggcaccag atacctgact cgtaatctgt    4620
aattgcttgt taatcaataa accgtttaat tcgtttcagt tgaactttgg tctctgcgta    4680 tttcttctt atctagtttc catggctacg tagataagta gcatggcggg ttaatcatta     4740
actacaagga accccctagtg atggagttgg ccactccctc tctgcgcgct cgctcgctca   4800
ctgaggccgg gcgaccaaag gtcgcccgac gcccgggctt tgcccgggcg gcctcagtga    4860
gcgagcgagc gcgcagagag ggacagatct tccatacccta ccagttctgc gcctgcagca   4920
atggcaacaa cgttgcccgg atccggtcgc gcgaattctt gaagacgaaa gggcctcgtg    4980
atacgcctat ttttataggt taatgtcatg ataataatgg tttcttagac gtcaggtggc    5040
acttttcggg gaaatgtgcg cggaaccccct atttgtttat ttttctaaat acattcaaat   5100
atgtatccgc tcatgagaca ataaccctga taaatgcttc aataatattg aaaaaggaag    5160
agtatgagta ttcaacattt ccgtgtcgcc cttattccct tttttgcggc attttgcctt    5220
cctgtttttg ctcacccaga aacgctggtg aaagtaaaag atgctgaaga tcagttgggt    5280
gcacgagtgg gttacatcga actggatctc aacagcggta agatccttga gagttttcgc    5340
cccgaagaac gttttccaat gatgagcact tttaaagttc tgctatgtgg cgcggtatta    5400
tcccgtgttg acgccgggca agagcaactc ggtcgccgca tacactattc tcagaatgac    5460
ttggttgagt actcaccagt cacagaaaag catcttacgg atggcatgac agtaagagaa    5520
ttatgcagtg ctgccataac catgagtgat aacactgcgg ccaacttact tctgacaacg    5580
atcggaggac cgaaggagct aaccgctttt ttgcacaaca tgggggatca tgtaactcgc    5640
cttgatcgtt gggaaccgga gctgaatgaa gccataccaa acgacgagcg tgacaccacg    5700
atgcctgcag caatggcaac aacgttgcgc aaactattaa ctggcgaact acttactcta    5760
gcttcccggc aacaattaat agactggatg gaggcggata agttgcagg accacttctg     5820 cgctcggccc ttccggctgg ctggtttatt gctgataaat ctggagccgg tgagcgtggg    5880
tctcgcggta tcattgcagc actggggcca gatggtaagc cctcccgtat cgtagttatc    5940
tacacgacgg ggagtcaggc aactatggat gaacgaaata gacagatcgc tgagataggt    6000
gcctcactga ttaagcattg gtaactgtca gaccaagttt actcatatat actttagatt    6060
gatttaaaac ttcattttta atttaaaagg atctaggtga agatccttt tgataatctc     6120 atgaccaaaa tcccttaacg tgagttttcg ttccactgag cgtcagaccc cgtagaaaag    6180
atcaaaggat cttcttgaga tcctttttt ctgcgcgtaa tctgctgctt gcaaacaaaa     6240
aaaccaccgc taccagcggt ggtttgtttg ccggatcaag agctaccaac tctttttccg    6300
aaggtaactg gcttcagcag agcgcagata ccaaatactg tccttctagt gtagccgtag    6360
ttaggccacc acttcaagaa ctctgtagca ccgcctacat acctcgctct gctaatcctg    6420
```

```
ttaccagtgg ctgctgccag tggcgataag tcgtgtctta ccgggttgga ctcaagacga      6480
tagttaccgg ataaggcgca gcggtcgggc tgaacggggg gttcgtgcac acagcccagc      6540
ttggagcgaa cgacctacac cgaactgaga tacctacagc gtgagctatg agaaagcgcc      6600
acgcttcccg aagggagaaa ggcggacagg tatccggtaa gcggcagggt cggaacagga      6660
gagcgcacga gggagcttcc aggggggaaac gcctggtatc tttatagtcc tgtcgggttt      6720
cgccacctct gacttgagcg tcgattttg tgatgctcgt caggggggcg gagcctatgg       6780
aaaaacgcca gcaacgcggc cttttttacgg ttcctggcct tttgctggcc ttttgctcac     6840
atgttctttc ctgcgttatc ccctgattct gtggataacc gtattaccgc ctttgagtga      6900
gctgataccg ctcgccgcag ccgaacgacc gagcgcagcg agtcagtgag cgaggaagcg      6960
gaagagcgcc tgatgcggta ttttctcctt acgcatctgt gcggtatttc acaccgcata      7020
tggtgcactc tcagtacaat ctgctctgat gccgcatagt taagccagta tacactccgc      7080
tatcgctacg tgactgggtc atggctgcgc cccgacaccc gccaacaccc gctgacgcgc      7140
cctgacgggc ttgtctgctc ccggcatccg cttacagaca agctgtgacc gtctccggga      7200
gctgcatgtg tcagaggttt tcaccgtcat caccgaaacg cgcgaggcag ctgcggtaaa      7260
gctcatcagc gtggtcgtga agcgattcac agatgtctgc ctgttcatcc gcgtccagct      7320
cgttgagttt ctccagaagc gttaatgtct ggcttctgat aaagcgggcc atgttaaggg      7380
cggttttttc ctgtttggtc actgatgcct ccgtgtaagg gggatttctg ttcatggggg      7440
taatgatacc gatgaaacga gagaggatgc tcacgatacg ggttactgat gatgaacatg      7500
cccggttact ggaacgttgt gagggtaaac aactggcggt atggatgcgg cgggaccaga      7560
gaaaaatcac tcagggtcaa tgccagcgct tcgttaatac agatgtaggt gttccacagg      7620
gtagccagca gcatcctgcg atgcagatcc ggaacataat ggtgcagggc gctgacttcc      7680
gcgtttccag actttacgaa acacggaaac cgaagaccat tcatgttgtt gctcaggtcg      7740
cagacgtttt gcagcagcag tcgcttcacg ttcgctcgcg tatcggtgat tcattctgct      7800
aaccagtaag gcaaccccgc cagcctagcc gggtcctcaa cgacaggagc acgatcatgc      7860
gcacccgtgg ccaggaccca acgctgcccg agatgcgccg cgtgcggctg ctggagatgg      7920
cggacgcgat ggatatgttc tgccaagggt tggtttgcgc attcacagtt ctccgcaaga      7980
attgattggc tccaattctt ggagtggtga atccgttagc gaggtgccgc cggcttccat      8040
tcaggtcgag gtggcccggc tccatgcacc gcgacgcaac gcggggaggc agacaaggta      8100
tagggcggcg cctacaatcc atgccaaccc gttccatgtg ctcgccgagg cggcataaat      8160
cgccgtgacg atcagcggtc cagtgatcga agttaggctg gtaagagccg cgagcgatcc      8220
ttgaagctgt ccctgatggt cgtcatctac ctgcctggac agcatggcct gcaacgcggg      8280
catcccgatg ccgccggaag cgagaagaat cataatgggg aaggccatcc agcctcgcgt      8340
cgcgaacgcc agcaagacgt agcccagcgc gtcggccgcc atgccggcga taatggcctg      8400
cttctcgccg aaacgtttgg tggcgggacc agtgacgaag gcttgagcga gggcgtgcaa      8460
gattccgaat accgcaagcg acaggccgat catcgtcgcg ctccagcgaa agcggtcctc      8520
gccgaaaatg acccagagcg ctgccggcac ctgtcctacg agttgcatga taaagaagac      8580
agtcataagt gcggcgacga tagtcatgcc ccgcgcccac cggaaggagc tgactgggtt      8640
gaaggctctc aagggcatcg gtcgacgctc tcccttatgc gactcctgca ttaggaagca      8700
gcccagtagt aggttgaggc cgttgagcac cgccgccgca aggaatggtg catgcaagga      8760
gatggcgccc aacagtcccc cggccacggg gcctgccacc atacccacgc cgaaacaagc      8820
```

```
gctcatgagc cgaagtggc gagcccgatc ttccccatcg gtgatgtcgg cgatataggc      8880
gccagcaacc gcacctgtgg cgccggtgat gccggccacg atgcgtccgg cgtagagctc      8940
tagagctcta gagaattctc atgtttgaca gcttatc                              8977
```

<210> SEQ ID NO 2
<211> LENGTH: 33
<212> TYPE: DNA
<213> ORGANISM: Artificial Sequence
<220> FEATURE:
<223> OTHER INFORMATION: Primer

<400> SEQUENCE: 2

```
gtgtaggcct cggatccagc caccatggga gtc                                  33
```

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3

```
ccatagagcc caccgcatcc cc                                              22
```

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4

```
tggtatcgtg gaaggactca                                                 20
```

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5

```
ccagtagagg cagggatgat                                                 20
```

<210> SEQ ID NO 6
<211> LENGTH: 536
<212> TYPE: PRT
<213> ORGANISM: Adeno-associated virus - 2
<220> FEATURE:
<223> OTHER INFORMATION: Rep 68

<400> SEQUENCE: 6

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80
```

```
Gln Phe Glu Lys Gly Glu Ser Tyr Phe His Met His Val Leu Val Glu
                 85                  90                  95

Thr Thr Gly Val Lys Ser Met Val Leu Gly Arg Phe Leu Ser Gln Ile
                100                 105                 110

Arg Glu Lys Leu Ile Gln Arg Ile Tyr Arg Gly Ile Glu Pro Thr Leu
                115                 120             125

Pro Asn Trp Phe Ala Val Thr Lys Thr Arg Asn Gly Ala Gly Gly Gly
130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
                180                 185                 190

Leu Thr His Val Ser Gln Thr Gln Glu Gln Asn Lys Glu Asn Gln Asn
                195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
                260                 265                 270

Ile Met Ser Leu Thr Lys Thr Ala Pro Asp Tyr Leu Val Gly Gln Gln
                275                 280                 285

Pro Val Glu Asp Ile Ser Ser Asn Arg Ile Tyr Lys Ile Leu Glu Leu
290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
                340                 345                 350

Phe Tyr Gly Cys Val Asn Trp Thr Asn Glu Asn Phe Pro Phe Asn Asp
                355                 360                 365

Cys Val Asp Lys Met Val Ile Trp Trp Glu Glu Gly Lys Met Thr Ala
                370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
                435                 440                 445

Glu Leu Thr Arg Arg Leu Asp His Asp Phe Gly Lys Val Thr Lys Gln
450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495
```

```
Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
        515                 520                 525

Arg Leu Ala Arg Gly His Ser Leu
    530                 535

<210> SEQ ID NO 7
<211> LENGTH: 621
<212> TYPE: PRT
<213> ORGANISM: Adeno-associated virus - 2
<220> FEATURE:
<223> OTHER INFORMATION: Rep 78

<400> SEQUENCE: 7

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320
```

```
Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
        515                 520                 525

Arg Tyr Gln Asn Lys Cys Ser Arg His Val Gly Met Asn Leu Met Leu
    530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
        595                 600                 605

Leu Val Asn Val Asp Leu Asp Asp Cys Ile Phe Glu Gln
    610                 615                 620

<210> SEQ ID NO 8
<211> LENGTH: 312
<212> TYPE: PRT
<213> ORGANISM: Adeno-associated virus - 2
<220> FEATURE:
<223> OTHER INFORMATION: Rep 40

<400> SEQUENCE: 8

Met Glu Leu Val Gly Trp Leu Val Asp Lys Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ser Leu Thr Lys Thr Ala Pro Asp Tyr Leu Val Gly Gln Gln
    50                  55                  60
```

-continued

```
Pro Val Glu Asp Ile Ser Ser Asn Arg Ile Tyr Lys Ile Leu Glu Leu
65                  70                  75                  80

Asn Gly Tyr Asp Pro Gln Tyr Ala Ala Ser Val Phe Leu Gly Trp Ala
            85                  90                  95

Thr Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Thr Val Pro
            115                 120                 125

Phe Tyr Gly Cys Val Asn Trp Thr Asn Glu Asn Phe Pro Phe Asn Asp
            130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
            165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
            195                 200                 205

Thr Thr Phe Glu His Gln Gln Pro Leu Gln Asp Arg Met Phe Lys Phe
            210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Lys Asp His Val Val Glu Val
            245                 250                 255

Glu His Glu Phe Tyr Val Lys Lys Gly Gly Ala Lys Lys Arg Pro Ala
            260                 265                 270

Pro Ser Asp Ala Asp Ile Ser Glu Pro Lys Arg Val Arg Glu Ser Val
            275                 280                 285

Ala Gln Pro Ser Thr Ser Asp Ala Glu Ala Ser Ile Asn Tyr Ala Asp
            290                 295                 300

Arg Leu Ala Arg Gly His Ser Leu
305                 310
```

<210> SEQ ID NO 9
<211> LENGTH: 397
<212> TYPE: PRT
<213> ORGANISM: Adeno-associated virus - 2
<220> FEATURE:
<223> OTHER INFORMATION: Rep 52

<400> SEQUENCE: 9

```
Met Glu Leu Val Gly Trp Leu Val Asp Lys Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ser Leu Thr Lys Thr Ala Pro Asp Tyr Leu Val Gly Gln Gln
    50                  55                  60

Pro Val Glu Asp Ile Ser Ser Asn Arg Ile Tyr Lys Ile Leu Glu Leu
65                  70                  75                  80

Asn Gly Tyr Asp Pro Gln Tyr Ala Ala Ser Val Phe Leu Gly Trp Ala
            85                  90                  95

Thr Lys Lys Phe Gly Lys Arg Asn Thr Ile Trp Leu Phe Gly Pro Ala
            100                 105                 110
```

```
Thr Thr Gly Lys Thr Asn Ile Ala Glu Ala Ile Ala His Thr Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Lys Asp His Val Glu Val
                245                 250                 255

Glu His Glu Phe Tyr Val Lys Lys Gly Gly Ala Lys Lys Arg Pro Ala
            260                 265                 270

Pro Ser Asp Ala Asp Ile Ser Glu Pro Lys Arg Val Arg Glu Ser Val
        275                 280                 285

Ala Gln Pro Ser Thr Ser Asp Ala Glu Ala Ser Ile Asn Tyr Ala Asp
    290                 295                 300

Arg Tyr Gln Asn Lys Cys Ser Arg His Val Gly Met Asn Leu Met Leu
305                 310                 315                 320

Phe Pro Cys Arg Gln Cys Glu Arg Met Asn Gln Asn Ser Asn Ile Cys
                325                 330                 335

Phe Thr His Gly Gln Lys Asp Cys Leu Glu Cys Phe Pro Val Ser Glu
            340                 345                 350

Ser Gln Pro Val Ser Val Val Lys Lys Ala Tyr Gln Lys Leu Cys Tyr
        355                 360                 365

Ile His His Ile Met Gly Lys Val Pro Asp Ala Cys Thr Ala Cys Asp
    370                 375                 380

Leu Val Asn Val Asp Leu Asp Asp Cys Ile Phe Glu Gln
385                 390                 395

<210> SEQ ID NO 10
<211> LENGTH: 4854
<212> TYPE: DNA
<213> ORGANISM: Artificial Sequence
<220> FEATURE:
<223> OTHER INFORMATION: Conditional expression system

<400> SEQUENCE: 10
tgggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctggagg ggtggagtcg tgacgtgaat tacgtcatag    180
ggttagggag gtcctgtatt agaggtcacg tgagtgtttt gcgacatttt gcgacaccat    240
gtggtcacgc tgggtattta agcccgagtg agcacgcagg gtctccattt tgaagcggga    300
ggtttgaacg cgcagccgcc atgccggggt tttacgagat tgtgattaag gtccccagcg    360
accttgacgg gcatctgccc ggcatttctg acagctttgt gaactgggtg ccgagaaggg    420
aatgggagtt gccgccagat tctgacatgg atctgaatct gattgagcag gcaccctga    480
```

-continued

```
ccgtggccga aagctgcag cgcgactttc tgacggaatg cgccgtgtg agtaaggccc      540
cggaggccct tttctttgtg caatttgaga agggagagag ctacttccac atgcacgtgc    600
tcgtggaaac caccggggtg aaatccatgg ttttgggacg tttcctgagt cagattcgcg    660
aaaaactgat tcagagaatt taccgcggga tcgagccgac tttgccaaac tggttcgcgg    720
tcacaaagac cagaaatggc gccggaggcg ggaacaaggt ggtggatgag tgctacatcc    780
ccaattactt gctccccaaa acccagcctg agctccagtg ggcgtggact aatatggaac    840
agtatttaag cgcctgtttg aatctcacgg agcgtaaacg gttggtggcg cagcatctga    900
cgcacgtgtc gcagacgcag gagcagaaca aagagaatca gaatcccaat tctgatgcgc    960
cggtgatcag atcaaaaact tcagccaggt acatggagct ggtcgggtgg ctcgtggaca   1020
aggggattac ctcggagaag cagtggatcc aggaggacca ggcctcatac atctccttca   1080
atgcggcctc caactcgcgg tcccaaatca aggctgcctt ggacaatgcg ggaaagatta   1140
tgagcctgac taaaaccgcc cccgactacc tggtgggcca gcagcccgtg gaggacattt   1200
ccagcaatcg gatttataaa attttggaac taaacgggta cgatccccaa tatgcggctt   1260
ccgtctttct gggatgggcc acgaaaaagt tcggcaagag gaacaccatc tggctgtttg   1320
ggcctgcaac taccgggaag accaacatcg cggaggccat agcccacact gtgcccttct   1380
acgggtgcgt aaactggacc aatgagaact ttcccttcaa cgactgtgtc gacaagatgg   1440
tgatctggtg ggaggagggg aagatgaccg ccaaggtcgt ggagtcggcc aaagccattc   1500
tcggaggaag caaggtgcgc gtggaccaga aatgcaagtc ctcggcccag atagacccga   1560
ctcccgtgat cgtcacctcc aacaccaaca tgtgcgccgt gattgacggg aactcaacga   1620
ccttcgaaca ccagcagccg ttgcaagacc ggatgttcaa atttgaactc acccgccgtc   1680
tggatcatga ctttgggaag gtcaccaagc aggaagtcaa agacttttc cggtgggcaa    1740
aggatcacgt ggttgaggtg gagcatgaat tctacgtcaa aaagggtgga gccaagaaaa   1800
gacccgcccc cagtgacgca gatataagtg agcccaaacg ggtgcgcgag tcagttgcgc   1860
agccatcgac gtcagacgcg gaagcttcga tcaactacgc agacaggtac caaaacaaat   1920
gttctcgtca cgtgggcatg aatctgatgc tgtttccctg cagacaatgc gagagaatga   1980
atcagaattc aaatatctgc ttcactcacg gacagaaaga ctgtttagag tgctttcccg   2040
tgtcagaatc tcaacccgtt tctgtcgtca aaaaggcgta tcagaaactg tgctacattc   2100
atcatatcat gggaaaggtg ccagacgctt gcactgcctg cgatctggtc aatgtggatt   2160
tggatgactg catctttgaa caataaatga tttaaatcag gtatggctgc cgatggttat   2220
cttccagatt ggctcgagga cactctctct gagctagctt cgtacggatc ctcggatcca   2280
gccaccatgg gagtcaaagt tctgtttgcc ctgatctgca tcgctgtggc cgaggccaag   2340
cccaccgaga caacgaaga cttcaacatc gtggccgtgg ccagcaactt cgcgaccacg   2400
gatctcgatg ctgaccgcgg gaagttgccc ggcaagaagc tgccgctgga ggtgctcaaa   2460
gagatggaag ccaatgcccg gaaagctggc tgcaccaggg gctgtctgat ctgcctgtcc   2520
cacatcaagt gcacgcccaa gatgaagaag ttcatcccag acgctgcca cacctacgaa   2580
ggcgacaaag agtccgcaca gggcggcata ggcgaggcga tcgtcgacat tcctgagatt   2640
cctgggttca aggacttgga gcccatggag cagttcatcg cacaggtcga tctgtgtgtg   2700
gactgcacaa ctggctgcct caagggcttt gccaacgtgc agtgttctga cctgctcaag   2760
aagtggctgc cgcaacgctg tgcgaccttt gccagcaaga tccagggcca ggtggacaag   2820
```

-continued

```
atcaaggggg ccggtggtga ctaagcggcc gcgtgtggaa agtccccagg ctccccagca    2880
ggcagaagta tgcaaagcat gcatctcaat tagtcagcaa ccaggtgtgg aaagtcccca    2940
ggctccccag caggcagaag tatgcaaagc atgcatctca attagtcagc aaccatagtc    3000
ccgcccctaa ctccgcccat cccgcccta actccgccca gttccgccca ttctccgccc    3060
catggctgac taatttttt tatttatgca gaggccgagg ccgcctcggc ctctgagcta    3120
ttccagaagt agtgaggagg cttttttgga ggcctaggct tttgcaaaaa gcttccatga    3180
aaaagcctga actcaccgcg acgtctgtcg agaagtttct gatcgaaaag ttcgacagcg    3240
tctccgacct gatgcagctc tcggagggcg aagaatctcg tgctttcagc ttcgatgtag    3300
gagggcgtgg atatgtcctg cgggtaaata gctgcgccga tggtttctac aaagatcgtt    3360
atgtttatcg gcactttgca tcggccgcgc tcccgattcc ggaagtgctt gacattgggg    3420
aattcagcga gagcctgacc tattgcatct cccgccgtgc acagggtgtc acgttgcaag    3480
acctgcctga aaccgaactg cccgctgttc tgcagccggt cgcggaggcc atggatgcga    3540
tcgctgcggc cgatcttagc cagacgagcg ggttcggccc attcggaccg caaggaatcg    3600
gtcaatacac tacatggcgt gatttcatat gcgcgattgc tgatccccat gtgtatcact    3660
ggcaaactgt gatggacgac accgtcagtg cgtccgtcgc gcaggctctc gatgagctga    3720
tgctttgggc cgaggactgc cccgaagtcc ggcacctcgt gcacgcggat ttcggctcca    3780
acaatgtcct gacggacaat ggccgcataa cagcggtcat tgactggagc gaggcgatgt    3840
tcggggattc ccaatacgag gtcgccaaca tcttcttctg gaggccgtgg ttggcttgta    3900
tggagcagca gacgcgctac ttcgagcgga ggcatccgga gcttgcagga tcgccgcggc    3960
tccgggcgta tatgctccgc attggtcttg accaactcta tcagagcttg gttgacggca    4020
atttcgatga tgcagcttgg gcgcagggtc gatgcgacgc aatcgtccga tccggagccg    4080
ggactgtcgg gcgtacacaa atcgcccgca gaagcgcggc cgtctggacc gatggctgtg    4140
tagaagtact cgccgatagt ggaaaccgac gccccagcac tcgtccgagg gcaaaggaat    4200
agagttctag aggatcataa tcagccatac cacagggccc atctgggcaa agattccaca    4260
cacggacgga cattttcacc cctctcccct catgggtgga ttcggactta aacaccctcc    4320
tccacagatt ctcatcaaga acaccccggt acctgcgaat ccttcgacca ccttcagtgc    4380
ggcaaagttt gcttccttca tcacacagta ctccacggga cacggtcagc gtggagatcg    4440
agtgggagct gcagaaggaa aacagcaaac gctggaatcc cgaaattcag tacacttcca    4500
actacaacaa gtctgttaat cgtggactta ccgtggatac taatgcgtg tattcagagc    4560
ctcgccccat tggcaccaga tacctgactc gtaatctgta attgcttgtt aatcaataaa    4620
ccgtttaatt cgtttcagtt gaactttggt ctctgcgtat ttctttctta tctagtttcc    4680
atggctacgt agataagtag catggcgggt taatcattaa ctacaaggaa ccctagtga    4740
tggagttggc cactccctct ctgcgcgctc gctcgctcac tgaggccggg cgaccaaagg    4800
tcgcccgacg cccgggcttt gcccgggcgg cctcagtgag cgagcgagcg cgca          4854
```

AAV-BASED CONDITIONAL EXPRESSION SYSTEM

CROSS-REFERENCE TO RELATED APPLICATIONS

This application is continuation of U.S. patent application Ser. No. 16/073,488, filed Jul. 27, 2108, now U.S. Pat. No. 11,155,831 B2, issued Oct. 26, 2021, which is a national stage application under 35 U.S.C. § 371, of International Application No. PCT/EP2017/051944, filed Jan. 30, 2017, which claims benefit of priority to European Application No. 16153329.4, filed Jan. 29, 2016, each of which is incorporated herein by reference in its entirety.

The present invention relates to a cell comprising (aa) a nucleic acid comprising in 5' to 3' direction (i) at least one adeno-associated virus (AAV) inverted terminal repeat (ITR) sequence; (ii) a promoter which is capable of being activated by (a) helper polypeptide(s) and optionally (a) helper polynucleotide(s); and (iii) a transgenic coding sequence under the control of said promoter of (aa)(ii); and (ab) a nucleic acid comprising in 5' to 3' direction (i) a promoter which is capable of being activated by said helper polypeptide(s) and optionally said helper polynucleotide(s); and (ii) at least one AAV rep gene coding sequence under the control of said promoter of (ab)(i); wherein said cell does not comprise an AAV cap gene and/or is not able to express any AAV cap gene product.

In this specification, a number of documents including patent applications and manufacturer's manuals is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Conditional expression of functionally relevant genes becomes an important molecular biological methodology in studying virus replication, screening for antiviral substances, detection of clinically relevant virus intentions and for propagation of viral vectors. Standard conditional gene expression systems need either administration of specific drugs, like doxycyclin for TetR-based systems or modification of the viral genome in case of Cre/loxP based systems (Rupp et al., J. Virol. 79, 486-94 (2005). Ruzsics Z, Koszinowski U H. Mutagenesis of the cytomegalovirus genome. pp. 41-61 (2008)).

AAV is small parvovirus, which was discovered as a contamination in Ad preparations (Atchison et al., Science 149, 754-756 (1965)) and accordingly coined as adeno-associated virus. As a member of the Parvoviridae family, AAV has a single stranded DNA of about 5 kb. Naturally, the lytic cycle of AAV occurs also when the cell is infected with AAV and Adenovirus at the same time (Alazard-Dany at al., PLoS Pathogens 5 (2009). McCarty at al., Annu Rev Genet. pp. 819-45 (2004), Myers et al., J. Virol. 35, 65-75 (1980)). AAV belongs to the *Dependovirus* genus. The genus name arose, because AAV infection alone is not lytic. After infection of cells with AAV, the virus delivers its genome into the host cell where it integrates into the cellular genome and remains latent. For initiating the lytic cycle of AAV, a superinfection with a helper virus, such as adenovirus (Ad) or herpesvirus, is required.

AAV infects animals as well as humans. Mainly AAV2, AAV3 and AAV5 were isolated from humans together with various Ad serotypes. AAV is not known to lead to any diseases in humans (Monahan & Samulski, Mol. Med. Today 6, 433-440 (2000)).

Decisions in the course of therapy of viral infections as well as development of novel antiviral agents entail a need for robust and reliable means and methods for determining presence of a certain virus as well as its responsiveness to a known or yet to be determined antiviral agent. Also, there is a continuous need for conditional expression systems.

The present invention addresses such needs, especially in the field of viruses from the Adenoviridae and Herpesviridae families.

The invention is illustrated with figures, briefly:

FIGS. 1A-1E show schematic representations and preferred sequences. FIG. 1A shows a schematic representation of a replicon of the invention. ITRs, inverted terminal repeats=AAV ori; REP, rep genes=non-structural proteins of AAV; GLuc, gaussia luciferase ORF; HYG, Hygromycin expression cassette; pBR332, bacterial vector). FIG. 1B shows an experimental setting of the AAV based replicon vector for the analysis. FIG. 1C shows a sequence of a preferred replicon vector of the invention. FIG. 1D shows sequences of preferred rep proteins. FIG. 1E shows a schematic representation of a replicon of the invention with further annotations.

FIGS. 2A-2B show induction of replicon response. FIG. 2A shows adenovirus induced replicon response upon transient transfection. FIG. 2B shows induction of replicon response of a stable cell line after Adenovirus infection.

FIGS. 3A-3B show luciferase expression after transfection or infection. FIG. 3A shows HSV-1 infection induced luciferase expression from the AAV replicon. FIG. 3B shows luciferese expression after infection of replicon containing stable cell line with HSV1.

FIGS. 4A-4C show induction conditions and amplification. FIG. 4A shows optimal induction of the AAV replicon requires productive helper virus infection. FIG. 4B shows amplification of the replicon vector upon AD5 infection. FIG. 4C shows amplification of the AAV replicon vector in LE2D8 cells upon HSV1 infection.

FIGS. 5A-5B show responses using ACV-sensitive and ACV-resistant HSV1 strains. FIG. 5A shows infection of ACV treated LE2D8 cells with ACV sensitive and ACV resistant HSV1 strains. FIG. 5B shows validation of resistance test of ACV sensitive- and ACV resistant HSV1 strains by endpoint dilution assay.

FIGS. 6A-B show applicability of AAV replicon based resistance test with clinical HSV2 isolates. LE2D8 cell line was treated with different concentrations of ACV following an infection with a sensitive HSV2 strain (FIG. 6A) or an ACV resistant HSV2 strain (FIG. 6B).

FIG. 7 shows human adenoviruses from different species induced replicon response. 293A cells were transfected with pAV-GLuc-Hyg and infected with Ad5 expressing the m-Cherry protein (ADChe) as a control and several different Ad serotypes or mock infected.

FIGS. 8A-8B show freezing and pre-seeding of already transfected cells allows AAV replicon induction by HSV-1 infection. 293A cells were transfected with pAV-GLuc-Hyg, frozen and pre-seeded onto a 96 well plate after 24 hours (FIG. 8A) and 48 hours (FIG. 8B) after transfection.

Figure 9A:
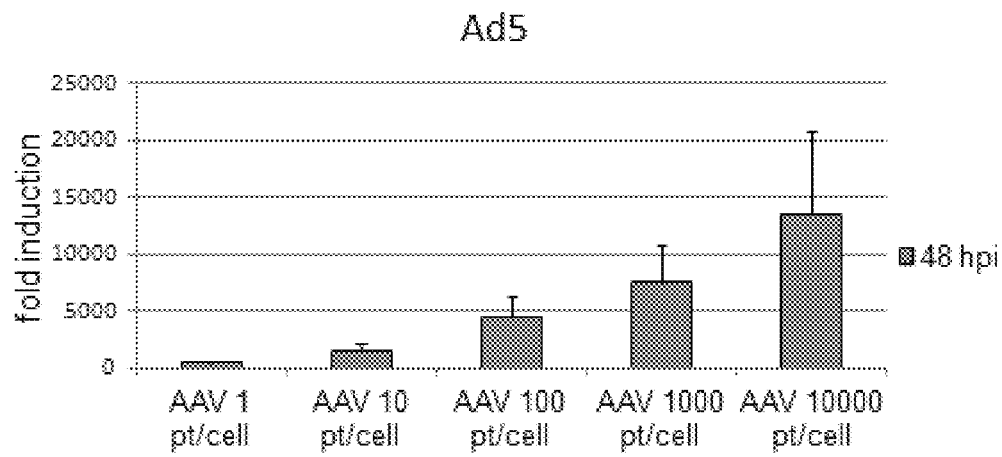
Figure 9B:
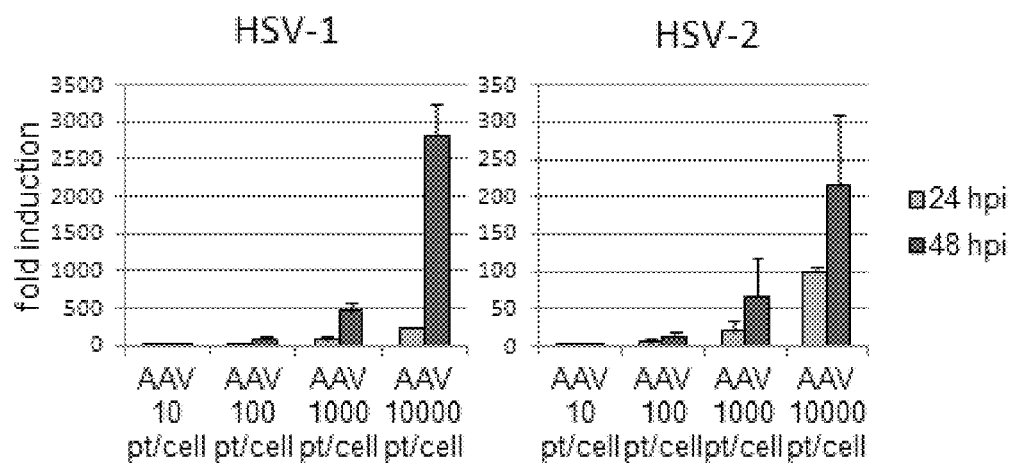
Figure 9C:
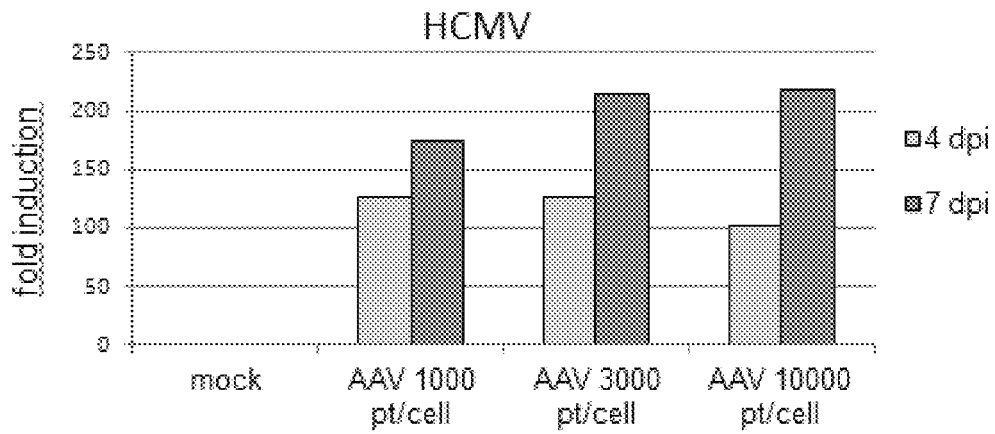

FIGS. 9A-9C show inducibility of the AAV replicon system transduction. FIG. 9A shows A549 cells transduced with rAAV Replicon particles at indicated densities (pt/cell) and infected with Ad5 at MOI 10, 6 hpt (hours post transduced) or kept MOCK infected. FIG. 9B shows Vero cells transduced with rAAV and after 6 hpt infected with either HSV-1 or HSV-2 at MOI 0.1. FIG. 9C shows rAAV Replicon particles transduced HFF cells infected with HCMV at MOI 1, 6 hpt and Sp was collected after 4 and 7 days p.i.

Accordingly, the present invention provides a cell comprising (aa) a nucleic acid comprising in 5' to 3' direction (i) at least one adeno-associated virus (AAV) inverted terminal repeat (ITR) sequence; (ii) a promoter which is capable of being activated by (a) helper polypeptide(s) and optionally (a) helper polynucleotide(s); and (iii) a transgenic coding sequence under the control of said promoter of (aa)(ii); and (ab) a nucleic acid comprising in 5' to 3' direction (i) a promoter which is capable of being activated by said helper polypeptide(s) and optionally said helper polynucleotide(s); and (ii) at least one AAV rep gene coding sequence under the control of said promoter of (ab)(i); wherein said cell does not comprise an AAV cap gene and/or is not able to express any AAV cap gene product.

It is understood that the present invention also provides a cell comprising (aa) a nucleic acid comprising in 5' to 3' direction (i) at least one adeno-associated virus (AAV) inverted terminal repeat (ITR) sequence; (ii) at least one promoter which is capable of being activated by (a) helper polypeptide(s) and optionally (a) helper polynucleotide(s); and (lii) a transgenic coding sequence under the control of said promoter of (aa)(ii); and (ab) a nucleic acid comprising in 5' to 3' direction (i) a promoter which is capable of being activated by said helper polypeptide(s) and optionally said helper polynucleotide(s); and (ii) at least one AAV rep gene coding sequence under the control of said promoter of (ab)(i); wherein said cell does not comprise an AAV cap gene and/or is not able to express any AAV cap gene product.

Said cell may be an in vitro cell, an ex vivo cell, a cell in culture or a cell of a cell line.

Said cell, in its widest sense, may be any vertebrate cell. Given that the present application focuses on applications in human and veterinary medicine, it is understood that, as described in more detail below, preferred cells are cells of mammalian, rodent, primate or human origin. Exemplary cells are apparent from the examples.

The term 'nucleic acid' has its art-established meaning and refers to a polycondensate of nucleotides. Preference is given to said nucleotides being deoxyribonucleotides. While not being preferred, it is nevertheless envisaged that 1, 2, 3, 4, 5, 6, 7, 8, 9 or 10 nucleotides, or at least 1%, at least 2%, at least 3%, at least 4%, at least 5%, at least 6%, at least 7%, at least 8%, at least 9% or at least 10% of the nucleotides are ribonucleotides and/or chemically modified nucleotides, said chemically modified nucleotides preferably being modified at the 2' position, for example 2'-methoxy or 2'-fluoro. Also envisaged are nucleic acids containing alternatives to the sugar phosphate backbone including peptide nucleic acids.

In terms of bases, the set of bases is preferably confined to A, G, C and T. Codon usage and/or codon preferences of said cell, to the extent known, may be considered in the design of the nucleic acids.

The nucleic acid of (aa) and/or the nucleic acid of (ab) may have been introduced into said cell by transient transfection. Said cell may be a cell of a stable cell line, either with regard to one or both of the nucleic acids (aa) and (ab).

As is apparent from the definition of nucleic acids (aa) and (ab) as provided above, respectively, use is made of structural elements of the genome of adeno-associated viruses (AAVs).

In more detail: inverted terminal repeat (ITR) sequences are known features of AAV viruses; see, for example, Wang et al., J. Mol. Biol. 250, 573-580 (1995). Exemplary ITR sequences can be found in the corresponding entries of the publicly available sequence databases. For example, the genomic sequence of AAV2 can be found in GenBank reference sequence NC_001401.2. For the purpose of sequence retrieval, GenBank version 209.0 of Aug. 15, 2015 may be used. In the mentioned reference sequence, two ITRs can be found at positions 1 to 145 and 4535 to 4679. Nucleic acids with a size of approximately up to 5.2 kb can be packaged into AAV capsids and contain 2 ITRs. Nucleic acids containing one ITR can be packaged as well. In exempli, this is the case for nucleic acids exceeding the packaging capacity of 5.2 kb for AAV2, which according to the publication by Wu et al., 2010 (Wu at al., Effect of genome size on AAV packaging. Mol. Ther. (2010) 18:80-86) can be packaged as 5'ITR truncated nucleic acids into AAV capsids. The packaged nucleic acids contain only one ITR in this case. The process for packaging of vector DNA into preformed capsids starts with the 3'ITR.

The presence of an ITR sequence is required in a nucleic acid sequence (aa). In a preferred embodiment, an ITR sequence is also present upstream of the promoter comprised in the nucleic acid sequence of (ab).

Either one of nucleic acids (aa) and (ab) requires a promoter which is capable of being activated by (a) helper polypeptide(s) and optionally helper polynucleotide(s). As is known in the art, transcription starts at promoters which, for being active, need to be in contact with one or more proteins, typically multi-protein complexes. In the present case, preference is given to promoters which occur in AAV. Preferred AAV promoters are disclosed further below and include the p40 wild type promoter, promoters which show at least 70%, at least 80%, at least 90%, at least 95%, at least 98% or at least 99% sequence identity to an AAV promoter and retain promoter activity, and promoters which show at least 70%, at least 80%, at least 90%, at least 95%, at least 98% or at least 99% sequence identity to the p40 wild type promoter and retain promoter activity. Promoter activity can be assessed without further ado, for example by performing the adenovirus induction assay disclosed in Example 3. The terms "p40" and "p40 promoter" include the above defined homologues of p40 wild type promoter. Structural and functional details of p40 are disclosed further below. Such promoters as well as any promoter in accordance with the present invention are responsive to (i) a AAV rep gene product and (ii) one or more helper polypeptides and optionally helper polynucleotides. Said one or more helper polypeptides, together with one or more rep proteins typically assemble to form a multi-protein complex which renders said promoter active. It has been shown that helper functions from human adenovirus can initiate virus replication, and hence recognize the ITRs and activate a promoter of AAV viruses from human and non-human species. For example the use of human adenovirus type 5 for replication of simian AAV1 was described here Xiao et al., J Virol. 73: 3994-4003 (1999). Further information about the recognition of ITRs and the initiation of replication can be found, for example, in Gavin et al., J. Virol. 73, 9433-9445 (1999). In particular, promoter and rep genes, respectively, can be chosen from different AAVs.

While this is the typical way of functioning of promoters originating from or being derived from adeno-associated viruses, it is understood that—as defined in accordance with the present invention—either promoter is capable of being activated by one or more helper polypeptides and optionally helper polynucleotide(s), i.e. also in the absence of any rep gene product. As a consequence, when making use of the present invention, a level of rep gene product will build up starting from a situation where no rep gene product is present at the beginning. Owing to the amount of rep gene product increasing over time, a further activation of either promoter occurs which entails amplified expression of the transgene (aa)(iii).

The terms "helper polypeptide" and "helper polynucleotide" are derived from the notion of a helper virus. For replication and transcription of the transgenic coding sequence to occur, certain helper functions need to be provided in trans. This can be done via helper virus, but does not have to be the case. In fact, in accordance with the present invention, said helper functions may be provided in the form of one or more polypeptides or nucleic acids encoding such one or more polypeptides, and, where applicable, one or more nucleic acid(s) providing said helper polynucleotide(s). Said helper polypeptides and helper polynucleotides may originate from or be derived from naturally occurring viruses such as an adeno-associated virus or a virus selected from the families of Adenoviridae and Herpesviridae. In the broadest sense, said helper polypeptide(s) are functionally defined by the requirement of being capable of activating the promoters as comprised in the nucleic acids (aa) and (ab), respectively, and preferably in conjunction with a rep protein encoded by the AAV rep gene of (ab)(ii).

Accordingly, it is understood that preference is given to helper polypeptides which bind to AAV promoters, i.e. promoters which occur in AAV. Moreover, it is understood that preferably said helper polypeptides activate said AAV promoters, i.e. they trigger or enhance transcription occurring from said promoters. It is known in the art that promoter-binding polypeptides of viruses from the families of Adenoviddae and Herpesviridae typically are capable of binding to and activating AAV promoters. In case of doubt, the skilled person can be determine without further ado in a promoter binding assay or promoter activation assay whether a given polypeptide encoded by a gene of a member of Adenoviridae or Herpesviddae is capable of binding and activating an AAV promoter.

Said one or more helper polypeptides and optionally helper polynucleotides are to be understood as the minimal version of a helper virus. In a preferred embodiment, said one or more helper polypeptides are polypeptides required for an induction of the lytic replication of an adeno-associated virus. In another preferred embodiment, said one or more helper polypeptides and optionally helper polynucleotides are products of the lytic cycle of helper virus. An especially preferred set of helper polypeptides is (a) the set comprising or consisting of the polypeptides encoded by the Adenovirus genomic loci E1, E2 and E4; or (b) the set comprising or consisting of Adenovirus proteins E1a, E1b-55K, E2a and E4orf6; see Samulski & Shenk, J. Virol. 62, 206-210 (1988). A preferred helper polynucleotide is Adenovirus VA. VA is an RNA (see Winter et al., J. Virol., 86, 5099-5109 (2012) and Matsushita et al., Journal of General Virology, 85, 2209-2214 (2004)). A preferred source of helper functions is Adenovirus 5. Another preferred set of helper polypeptides is the set comprising or consisting of HSV-1 proteins UL5, UL8, UL52 and UL29, the former three forming the helicase/primase complex and the latter encoding the single-stranded DNA-binding protein; see also Weindler & Heilbronn, J. Virol. 65, 2476-2483 (1991). The sequences of these helper polypeptides can be retrieved from sequence data bases like GenBank, especially the version of GenBank identified in this document. Generally, the genomic sequences of viruses from which the helper functions originate are annotated and contain information about the sequences of the individual genes providing said helper functions. This applies, for example, to the genomic sequences of HSV-1 and Ad5 as referenced further below.

It is understood that instead of these specific helper polypeptides and polynucleotides, functional homologues may be used. Functional homologues exhibit at least 80%, at least 90%, at least 95%, at least 98% or at least 99% sequence identity to the respective parent polypeptide or polynucleotide, respectively, as identified above. Said homologues retain their helper function, i.e. the capability to trigger transcription of the transgenic coding sequence as defined herein above. Preferably, said capability to trigger transcription is at least 10%, at least 20%, at least 30%, at least 40%, at least 50%, at least 60%, at least 70%, at least 80% or at least 90% of the capability of the parent sequence to trigger transcription.

Further alternatives to said polypeptides and, where applicable, polynucleotides, which alternatives meet the functional requirement as laid down in the first aspect can be determined by the skilled person without further ado. For example, a protein coding sequence under the control of said promoter may be combined with one or more helper polypeptides and optionally furthermore with one or more rep gene products. An increase in the amount of protein product is indicative of said promoter being capable of being activated by one or more helper polypeptides, one or more rep proteins being optionally present. Said protein under the control of said promoter may be a transgenic coding sequence in the sense of the first aspect of the present invention.

Further exemplary information about helper functions can be found, for example, in McPherson et al., Virology 147, 217-222 (1985).

The cell in accordance with the first aspect of the present invention is not a means of providing AAV particles. This is expressed by the requirement of newly made structural proteins VP1, VP2 and VP3 being absent. In particular, said cell does not comprise a cap gene and/or is not able to express any AAV cap gene product. What is conceivable, though, is that for the purpose of making said cell, transduction is effected with AAV particles. Said particles would comprise the structural proteins VP1, VP2 and VP3; however, neither said particles nor the obtained cell would be capable of newly making said structural proteins or any cap gene products.

Surprisingly, and despite the absence of a cap gene, the cell of the invention provides a functioning conditional expression system.

The cell in accordance with the first aspect is a means for expressing a transgenic coding sequence in response to one or more helper polypeptides. As will be apparent from preferred applications of the present invention as disclosed below, a helper polypeptide and, where applicable, a helper polynucleotide, may be provided by viruses, especially pathogenic viruses of relevance for human and veterinary medicine. Presence of a virus capable of providing helper function. i.e. helper polypeptides, will entail expression of the transgenic coding sequence. Presence and amount of the translation product of the transgenic coding sequence is a means of determining presence, amount and/or activity of the helper. Since amount and/or activity of the helper may be influenced by the presence of antiviral agents, presence and/or activity of antiviral agents may also be determined by using the cell in accordance with the first aspect of the present invention.

Such cell is also referred to as "conditional expression system" herein, and the nucleic acid(s) comprised in said cell as "replicon vector". The advantage of the conditional expression system is that it can be activated by both adenovirus infections and herpesvirus infections. Yet, the conditional expression system does not exhibit any homology either to adenovirus or herpesvirus genomes. This excludes any unwanted homologous recombination between the replicon vector and the virus of interest. Difficulties which may arise in case of homology are described, for example, in Mohr et al., PLoS Pathog 8(6): e1002728. doi:10.1371/journal.ppat.1002728 (2012). Furthermore, the conditional expression system performs well in both episomal and integrated state; see the corresponding preferred embodiment disclosed further below. A key feature of the conditional expression system is that its activation involves both (i) replication of the replicon vector and (ii) transcription and, where applicable, translation of the transgenic coding sequence.

In a second aspect, the present invention provides a kit comprising: (a) (aa) a nucleic acid comprising in 5' to 3' direction (I) at least one adeno-associated virus (AAV) inverted terminal repeat (ITR) sequence; (ii) a promoter which is capable of being activated by the helper polypeptide(s) and optionally, the helper polynucleotide(s) of (b); (iii) a transgenic coding sequence under the control of said promoter of (aa)(ii); (ab) a nucleic acid comprising in 5' to 3' direction (i) a promoter which is capable of being activated by said helper polypeptide(s) and optionally, the helper polynucleotide(s) of (b); (ii) at least one AAV rep gene coding sequence under the control of said promoter of (ab)(i); and optionally (b) one or more nucleic acids encoding in expressible form said helper polypeptide(s) and optionally providing said helper polynucleotide(s); wherein said kit neither comprises the AAV cap gene nor means to express any AAV cap gene product.

In its broadest definition, the kit according to the second aspect of the present invention comprises the two nucleic acids (aa) and (ab) as defined in relation to the first aspect. Optionally, said kit comprises one or more nucleic acids encoding in expressible form the above discussed helper polypeptide(s) and, where applicable, providing said helper polynucleotide(s). Accordingly, and in one preferred embodiment, said kit comprises three distinct types of nucleic acids (aa), (ab) and (b). A cell as required by the first aspect may be comprised in the kit according to the second aspect, but does not have to.

To the extent said kit does comprise a cell, it is preferred that said nucleic acids of (aa) and (ab) are comprised in said cell, wherein said cell does not comprise a AAV cap gene and/or is not able to express any AAV cap gene product. The reasons therefor are those explained above in relation to the first aspect: the present invention does not intend to provide means and methods for producing AAV particles.

Preferably, said cell does not comprise any one of an AAV cap gene or nucleic acids coding for any one of VP1, VP2 or VP3. The same preferred embodiment applies mutatis mutandis to the kit according to the second aspect described in more detail below.

Preferred transgenic coding sequences in accordance with both the first and second aspect of the present invention are those transgenic coding sequences which, upon expression, produce a transgenic protein, preferably a transgenic protein generating a detectable signal. Examples include luciferases and other reporter genes known in the art including fluorescent reporters such as EGFP and RFP.

A particularly preferred embodiment of either aspect of the present invention relates to a transgene encoding sequence encoding a luciferase, the promoter in the nucleic acid (aa) being AAV p40 and the promoter in the nucleic acid (ab) being AAV p5 promoter in combination with the p19 promoter. In the alternative, p40 may be used for either nucleic acid. In that case, preference is given to helper polypeptide(s) or helper virus(es), respectively, which can directly activate p40.

Further preferred transgenes include fluorescent proteins such as GFP and transgenes the gene product of which can be detected by enzymatic assays, such as beta-galactosidase, S-Glucuronidase (GUS) and alkaline phosphatase (AP).

The term "originating from" refers to a composition of matter, in particular a polypeptide or nucleic acid, which is identical to its occurrence in the corresponding natural source.

The term "is derived from" has a more generic meaning in the sense that it allows for modifications which render said composition of matter different from its natural occurrence while maintaining, at least to a substantial degree, function. Maintenance of a substantial degree of function preferably refers to maintenance of at least 10%, at least 20%, at least 30%, at least 40%, at least 50%, at least 60%, at least 70%, at least 80%, at least 90% function, or full maintenance (100%) of function or activity.

In a preferred embodiment of both the set of the first aspect and the kit of the second aspect. (i) the sequences of nucleic acids of (aa) and (ab) are comprised in a single circular nucleic acid, wherein preferably the sequence of the nucleic acid of (ab) is positioned within the sequence of the nucleic acid of (aa) after (aa)(i) and before (aa)(ii) in 5' to 3' direction; (ii) the sequences of the nucleic acids of (aa) and (ab) are each comprised in a separate circular nucleic acid; (iii) the sequences of the nucleic acids of (aa) and (ab) are comprised in a single linear nucleic acid, wherein preferably the sequences of the nucleic acid of (ab) is positioned within the sequence of the nucleic acid of (aa) after (aa)(i) and before (aa)(ii) in 5' to 3' direction; or (iv) the sequences of the nucleic acids of (aa) and (ab) are each comprised in a separate linear nucleic acid.

Particular preference is given to circular nucleic acids, i.e. options (I) and (ii). Among these two preferred options, option (i), i.e. a single circular nucleic acid, is especially preferred. This is inter alia because adverse responses of host cells are generally stronger against linear DNA as compared to circular DNA.

In another preferred embodiment the sequences of the nucleic acids of (aa) and (ab) are comprised in a single linear nucleic acid, wherein preferably the sequences of the nucleic acid of (ab) is positioned within the sequence of the nucleic acid of (aa) after (aa)(i) and before (aa)(ii) in 5' to 3' direction, and the transgenic coding sequence (aa)(iii) is followed by an adeno-associated virus (AAV) inverted terminal repeat (ITR) sequence in inverted orientation.

Such single nucleic acid is preferably comprised in a virion of the invention.

Circular nucleic acids (such as those of options (i) and (ii))—entail a specific technical effect. In particular, circular nuclear acids, once present in a cell, are amplified by the cellular machinery.

Linear nucleic acids on the other hand, i.e. linear nucleic acids in accordance with options (lii) and (iv), are capable of being stably integrated into the genome of the host cell.

In either case, it is preferred that nucleic acid(s) of the invention do not encode a fusion protein of rep with the product of said transgenic coding sequence. In fact, the configuration of above option (i) with sequence (ab) between (aa)(i) and (aa)(ii) does not encode a fusion protein.

In a further preferred embodiment of first and second aspect, (i) the sequences of the nucleic acids of both (aa) and (ab) are comprised in the genomic DNA of said cell; or (ii) the sequence of the nucleic acid of (ab) is comprised in the genomic DNA of said cell.

In a further preferred embodiment, (i) the promoter of (aa)(ii) is selected from the group consisting of AAV promoters p40, p5, p19 and late promoters from a virus naturally encoding said helper polypeptide(s), preferably the AAV p40 promoter; and/or (ii) the promoter of (ab)(i) is selected from promoters p5, p19 and p40, preferably p5 or p19, and even more preferably a combination of the p5 and the p19 promoter. Examples of the mentioned late promoters are adenovirus major late promoter (MLP), UL94-promoter from HCMV and UL16 promoter from HSV-1.

Analogous to what is stated above in relation to the p40 promoter, the terms "p5" and "p19" as used herein embrace functional homologies thereof. In particular, promoters which show at least 70%, at least 80%, at least 90%, at least 95%, at least 98% or at least 99% sequence identity to the p5 and the p19 wild type promoter, respectively, and retain promoter activity, are embraced.

p5 is located between positions 190 and 310 of the AAV2 genome sequence disclosed in the above mentioned GenBank database entry. Further information about the p5 promoter can be found, for example, in Chang et al., J. Virol. 63, 3479-3488 (1989). Promoters p19 and p40 are located at positions 720 to 873 and 1700 to 1853, respectively, of the AAV2 genome sequence as disclosed in the above mentioned GenBank entry NC_001401.2. Further information about either promoter can be found in McCarty, J. Virol. 65, 2936-2945 (1991).

In a preferred embodiment, the p40 promoter comprises an extended rep-binding site and/or extends from the above-mentioned position 1700 until position 2287 of the AAV2 genome. Positions 1854 to 2287 comprise the 5' UTR which in turn includes a small intron (positions 1907 to 2227). The 5' UTR is preferably present when full and tight regulation is desired.

In more detail, and without wishing to be bound by a particular theory, activation of the p40 promoter by helper particular polypeptides and helper polynucleotides such as VA RNAs involves activation/derepression of the p5 and p19 promoter, which in turn lead to the expression of rep proteins activating the p40 promoter.

The molecular mechanism for two preferred adenovirus helper polypetides is as follows:

Adenovirus E1a: binding of E1a:p300:YY1 to the p5 promoter induces the exposure of the YY1 activation domain and leads to activation of the p5 promoter driving rep expression, leading to the activation of the p19 and p40 promoter. In the repressed state, the YY1 transcription factor is in proximity to the rep protein bound to the p5rep binding element, which leads to an inhibition of the p5 promoter. (Shi et al., Cell. 1991 Oct. 18; 67(2):377-88. PMID: 1655281).

Adenovirus E2a: The adeno-associated virus P5 promoter and the adenovirus E1a and E2a early and major late promoters respond to the DNA-binding protein by increases in expression ranging from 6- to 27-fold (Chang, and Shenk, J. Virol. (1990), 64:2103-2109).

The preferred promoter elements are as follows.

The regulation and induction of the p40 promoter involves intact p40 promoter structure and preferably in addition elements/sequences of the p5 and p19 promoter.

The p5 promoter regulates the expression of the rep78 and its alternatively splice variant p68. Rep78 and Rep68 are capable of binding to a linear DNA sequence that is contained within a 25-bp sequence of the A stem of the adeno-associated virus (AAV) terminal repeat proximal to the B and C palindromes (McCarthy et al., J. Virol. (1994), 68:4988-4997). The p5 promoter contains crucial transcription factor binding sites for YY1 and the major late transcription factor MLTF (reference Shi et al. 1991). The several rep-binding elements in the ITR (A-stem rep binding site), the p5, and the p19 promoter respectively, are important to mediate rep-mediated promoter repression of the p5 during latency. In turn, rep protein binding sites in the ITR and p5 and the p19 promoter act as transactivators for p19 and p40 promoter activity during productive production in the presence of adenovirus helper virus (Pereira et al, J Virol. (1997), 71:1079-88). The Rep binding sequence within the p5 promoter is located between the YY1 initiator sequence and the TATA binding site (McCarthy et al., 1994). The rep-mediated activity of the p19 promoter was effected by two sites mainly, the SP1-50 and CArG-140 sites. Rep-induction of the p40 promoter depended on the SP1-50 and TATA-30 sites and the previously identified p19 CArG-140 site (Ph.D. thesis by Daniel Francis Lackner; University of Florida Digital Collections). The p19 promoter contains several transcription factor binding sites located upstream of the transcription start site: SP1-50. GGT-110, SP1-130, cArG-140. The -50, -110, and -130 sites have been found to bind SP1, whereas the -140 site binds SRE transcription factor (Pereira and Muzyczka, J. Virol. (1997a), 71:1747-1756). The p40 promoter contains an AP1-40, SP1-50, GGT-70, and MLTF-100 site (Pereira and Muzyczka, J. Virol. (1997b), 71:4300-4309).

As noted above, the p40 promoter preferably contains an extended rep-binding site, which increases the mRNA splicing from the AAV intron. The construct of the invention therefore preferably contains the full-length p40 promoter extending until nt 2287 (Qiu and Pintel, Mol Cell Biol. (2002), 22:3639-52).

Alternative or synthetic promoters derived from AAV promoters preferably contain at least the transcription factor binding sites and rep-binding sites including the p40 promoter proximal sites required for efficient splicing of the AAV intron.

In a further preferred embodiment, at least one AAV rep gene coding sequence of (ab)(ii) encodes the AAV Rep78 and/or the AAV Rep68 polypeptide, wherein preferably the at least one AAV rep gene coding sequence of (ab)(ii) further encodes the AAV Rep52 and/or AAV Rep40 polypeptide.

GenBank entries for the mentioned rep proteins (GenBank version 209.0) are as follows: YP_680422.1 (Rep68), YP_680423.1 (Rep78), YP_680424.1 (Rep40) and YP_680425.1 (Rep52); see also FIG. 1D and SEQ ID NOs: 6 to 9. The role of rep protein in AAV replication is well-known in the art described, for example, in Labow et al., J. Virol. 60, 251-258 (1986); Hermonat et al., J. Virol. 51, 329-339 (1984); Ni et al., J. Virol. 68, 1128-1138 (1994); and Ryan et al., J. Virol. 70, 1542-1553 (1996). It is understood that instead of the above defined specific rep proteins, functional homologues may be used. Functional homologues exhibit at least 80%, at least 90%, at least 95%, at least 98% or at least 99% sequence identity to the above identified specific sequences and are capable of performing replication. Preferably, replication activity is at least 10%, at least 20%, at least 30%, at least 40%, at least 50%, at least 60%, at least 70%, at least 80% or at least 90% of the parent protein which is defined by the specific sequence referred above.

In a further preferred embodiment of both first and second aspect of the present invention, the nucleic acid of (b), to the extent present, is comprised (i) in a helper virus; or (ii) said cell furthermore comprises said nucleic acid of (b).

As noted above, one or more helper polypeptides are minimal versions of a helper virus. Item (i) of this preferred embodiment introduces the requirement of a helper virus as a means of providing said helper polypeptide(s). A helper virus may be functionally defined as a virus capable of infecting the cell according to the present invention and providing gene products which induce the replication of the replicon vector according to the invention and transcription of the transgenic coding sequence. Helper functions may be provided by viruses which are to be detected or characterized; see preferred applications of the invention as disclosed further below.

In a further preferred embodiment, the nucleic acid sequence of (aa) comprises two AAV inverted terminal repeat sequences, wherein the second inverted terminal repeat sequence is positioned after the transgenic sequence of (aa)(iii) and in inverted orientation.

In another preferred embodiment, the helper polypeptide(s) and, wherein applicable, the helper polynucleotide(s) of (b) originate from a virus selected from Adenovirdae and Herpesviridae. Especially preferred viruses in relation to this embodiment are Adenovirus 5 (Ad5), HSV-1, HSV-2 and HCMV. The genomic sequences of these viruses can be found in the databases mentioned above. E.g., Ad5 in the database entry AC_000008.1 and HSV-1 in the database entry NC_001806.2.

As mentioned above, in a preferred embodiment said cell is a eukaryotic, mammalian, rodent, primate or human cell.

In an especially preferred embodiment, said helper virus is HCMV or said one or more helper polypeptides originate from or are derived from HCMV, and said cell is a human foreskin fibroblast (HFF) or an MRC5 cell.

In a further especially preferred embodiment, said helper virus is an adenovirus and said cell is a 293 cell.

In a further especially preferred embodiment, said helper virus is an HSV-1 or HSV-2 and said cell is a HFF cell.

In a further especially preferred embodiment, said helper virus is an HSV-1 or HSV-2 and said cell is a 293 cell.

In a further especially preferred embodiment, said helper virus is an HSV-1 or HSV-2 and said cell is a Vero cell.

In a particularly preferred embodiment of the kit in accordance with the second aspect, (a) said cell is provided in a vessel; (b) said cell is provided in multiple instances in the wells of a multiwell plate; and/or (c) said kit comprises a manual containing instructions, preferably instructions for performing the methods of the invention as disclosed further below.

Embodiment (b) within the above described preferred embodiment relates to an implementation of the kit which is preconfigured for high throughput applications. For example, the cells as comprised in the wells of said multiwell plate may be stored at low temperature, preferably below or at −80° C. Prior to their use, the cells are retrieved from the freezer and thawed. Envisaged assays for which such multiwell plates may be employed include the addition of clinical samples for each well, an incubation for a predetermined amount of time such as two days, and subsequence detection of a detectable signal, for example a luminescent signal generated by luciferase, luciferase being, as mentioned above, a preferred transgenic coding sequence.

Similarly, also in accordance with embodiment (a), which is designed for individual tests which are not in high-throughput format, said cell may be provided or stored at low temperature, preferably below or at −80° C.

The conditional expression system as defined by first and second aspect as well as preferred embodiments thereof makes a host of applications accessible. Applications include those of further aspects below.

In a third aspect, the present invention provides a method of determining whether a virus, preferably a pathogenic virus and/or preferably selected from Adenoviridae and Herpesviridae, is inhibited by an antiviral agent, said method comprising bringing into contact the kit of the first aspect with a sample comprising said virus, wherein said contacting is effected (i) in the presence of said antiviral agent and (ii) in its absence, wherein a greater amount of product of the transgenic coding sequence as defined in accordance with said kit or virion, respectively, in case (ii) is indicative of said virus being inhibited by the said agent.

To explain further, it turned out that certain pathogenic viruses are resistant to treatment with antiviral agents such as aciclovir, whereas others are not. For the purpose of differential diagnostics and as an aid in therapeutic decisions the method of the third aspect may be employed in order to determine whether the pathogenic agent as comprised in a given sample is resistant to a given antiviral agent such as aciclovir or not.

In a preferred embodiment of the third aspect, and especially to the extent aciclovir is used, a member of the Herpesviridae is considered resistant if the amount of transgenic protein produced or the signal emitted by said transgenic protein in the presence of 20 Ng/ml aciclovir is at least 30%, at least 40%, at least 50%, at least 60% or at least 70%, preferably 50% of the amount or signal intensity, respectively, in the absence of aciclovir. In a further preferred embodiment of the third aspect, and especially to the extent aciclovir is used, a member of the Herpesviridae is considered resistant if the amount of transgenic protein produced or the signal emitted by said transgenic protein in the presence of 100 µg/ml aciclovir is at least 10%, at least 20%, at least 30%, at least 40% or at least 50%, preferably at least 30% of the amount or signal intensity, respectively, in the absence of aciclovir.

In a modified implementation, a candidate antiviral agent may be used instead of an established antiviral therapeutic, thereby making available means and methods of identifying and/or validating novel antiviral agents. Accordingly, the present invention, in an aspect related to the third aspect, provides a method of determining whether a candidate antiviral agent has antiviral activity against a virus, said virus preferably being selected from Adenoviridae and Herpesviridae, said method comprising bringing into contact kit of the first aspect with said virus, wherein said contacting is effected (I) in presence of said candidate antiviral agent and (ii) in its absence, wherein the greater amount of product of the transgenic coding sequence defined in accordance with the kit in case (ii) is indicative of said candidate antiviral agent having antiviral activity against said virus. In that implementation, said virus is preferably a laboratory strain of a virus selected from Adenoviridae. Herpesviridae or adeno-associated viruses. In the alternative, a clinical isolate may be used. Related thereto is also the fifth aspect disclosed further below.

In a fourth aspect, the present invention provides a method for conditional gene expression comprising introducing into the cell as defined in the first aspect, one or more nucleic acids encoding one or more helper polypeptide(s)

and, optionally providing one or more helper polynucleotide(s) as defined in any of the preceding embodiments, thereby expressing the product encoded by said transgenic coding sequence.

Said introducing may be by transient transfection or stable transfection. Also, stable transfection may be used for a first subset of said one or more nucleic acids, and transient transfection for a second subset of said one or more nucleic acids.

In a fifth aspect, the present invention provides a method of detecting and/or quantifying infectious virus, said virus preferably being selected from Adenoviridae and Herpesviridae, said method comprising bringing into contact a cell in accordance with the first aspect with a sample comprising or suspected of comprising said infectious virus, wherein presence and/or amount of product of the transgenic coding sequence as defined in accordance with said cell, is indicative of the presence and/or the amount of said infectious virus.

Preferably, said sample is a sample taken from an individual such as a human. Preferably, said sample is a tissue sample such as a tissue biopsy or a bodily fluid. Preferred bodily fluids include bronchoalveolar lavage (BAL), a herpes blister and the fluid contained therein.

Instead of detecting and/or quantifying a virus selected from the families of Adenoviridae and Herpesviridae, said method of the sixth aspect may analogously be applied for the purpose of detecting and/or quantifying replication competent viral vectors based on a virus selected from the families of Adenoviridae and Herpesviridae.

In a sixth aspect, the present invention provides a method for identifying a compound having antiviral activity against a virus, said virus preferably being selected from Adenoviridae and Herpesviridae, said method comprising the steps of: (a) introducing into cells of a population of cells as defined in any of the preceding embodiments the nucleic acid(s) encoding one or more helper polypeptide(s) and, optionally providing one or more helper polynucleotide(s) as defined in any one of the preceding embodiments; (b) determining the amount of the product encoded by said transgenic coding sequence of (aa)(iii) expressed by the cell population of step (a) after said introducing; (c) contacting a population of cells as defined in any one of the preceding embodiments with the compound to be tested; (d) Introducing into cells of the cell population of step (c) said nucleic acid(s) defined in step (a); (e) determining the amount of the product encoded by said transgenic coding sequence expressed by the cell population of step (d) after said introducing; (f) comparing the amount of said product determined in step (b) with the amount of said product determined in step (e), wherein less product determined in step (e) relative to the product determined in step (b) indicates that the tested compound has antiviral activity.

Said introducing may be by transient transfection or stable transfection. Also, stable transfection may be used for a first subset of said one or more nucleic acids, and transient transfection for a second subset of said one or more nucleic acids.

In a further aspect, the present invention provides a virion comprising a nucleic acid comprising in 5' to 3' direction (i) an adeno-associated virus (AAV) inverted terminal repeat (ITR) sequence; (ii) at least one promoter which is capable of being activated by (a) helper polypeptide(s) and optionally (a) helper polynucleotide(s), preferably the AAV promoter p5 and the AAV promoter p19; (iii) at least one AAV rep gene coding sequence under the control of said promoter of (ii); (iv) a promoter which is capable of being activated by said helper polypeptide(s) and optionally said helper polynucleotide(s), preferably the AAV promoter p40; (v) a transgenic coding sequence under the control of said promoter of (iv); (vi) a polyadenylation site; and (vii) an adeno-associated virus (AAV) inverted terminal repeat (ITR) sequence; wherein said virion does not comprise an AAV cap gene and/or is not able to express any AAV cap gene products.

The term "virion" has its art-established meaning and relates to a virus particle. Preferably, said virus particle is outside any cell. Generally, a virion comprises or consists of one or more nucleic acid molecules which are surrounded by a capsid, said capsid typically comprising or consisting of virus encoded proteins.

The nucleic acid comprised in said virion exhibits those features which are disclosed further above in relation to the cell of the invention and the kit of the invention. Preferred embodiments of the cell and the kit of the invention define preferred embodiments of the virion of the invention, to the extent applicable.

In a preferred embodiment, said virion consists of the nucleic acid defined above and said capsid proteins.

Genes encoding capsid protein can be obtained from AAV1, AAV2, AAV3, AAV4, AAV5, AAV6, AAV7, AAV8, AAV9 and rhAAV10. Capsid proteins may be synthetic and contain peptide insertions or can be obtained by DNA family shuffling, containing a mixture of cap genes from different AAV serotypes; see, for example, Michelfelder S, Varadi K, Raupp C, Hunger A. Körbelin J, Pahrmann C. Schrepfer S, Müller O J, Kleinschmidt J A, Trepel M. PLoS One. 2011; 6(8):e23101; Müller O J, Kaul F, Weitzman M D, Pasqualini R, Arap W, Kleinschmidt J A, Trepel M. Nat Biotechnol. 2003 September; 21(9):1040-6; and Grimm D, Lee J S, Wang L, Desal T, Akache B, Storm T A, Kay M A. J Virol. 2008 June; 82(12):5887-911.

Preferred capsid proteins are VP1, VP2 and VP3.

Typically, the capsid proteins are encoded by the cap gene of AAV. It is important to note that the virion typically comprises a cap gene product, however, as defined above and consistent with the other aspects of the invention, the virion of the invention does not comprise an AAV cap gene and/or is not able to express any AAV cap gene product.

Preferred capsid proteins are VP1, VP2 and VP3.

The virion of the invention is preferably an infectious virion. Accordingly, it is able to infect cells, including cells which are already infected by another virus, said other virus preferably being selected from Adenoviridae and Herpesviridae.

As regards the topology of the nucleic acid comprised in the virion of the invention, preference is given to linear nucleic acid. A particularly preferred linear nucleic acid is shown in SEQ ID NO: 10. SEQ ID NO: 10 corresponds to positions 1 to 4854 of SEQ ID NO: 1.

The virion of the invention is a preferred transport vehicle for the nucleic acids comprised in said virion.

As regards the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E. H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

Figure 1A:
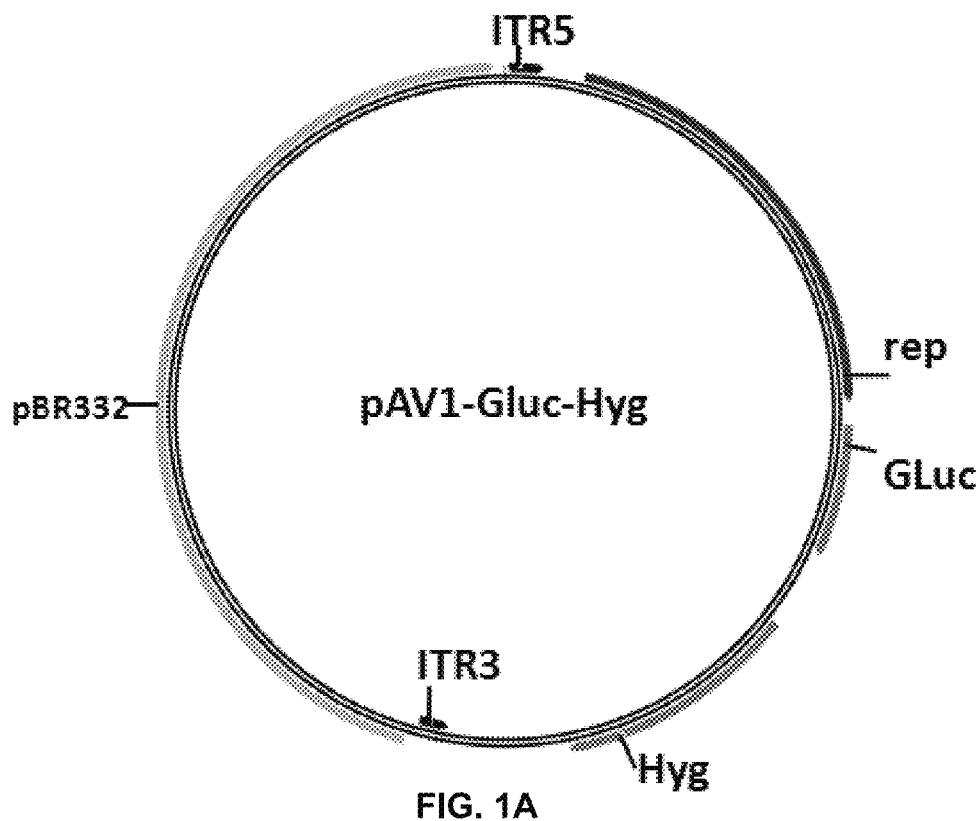
Figure 1B:
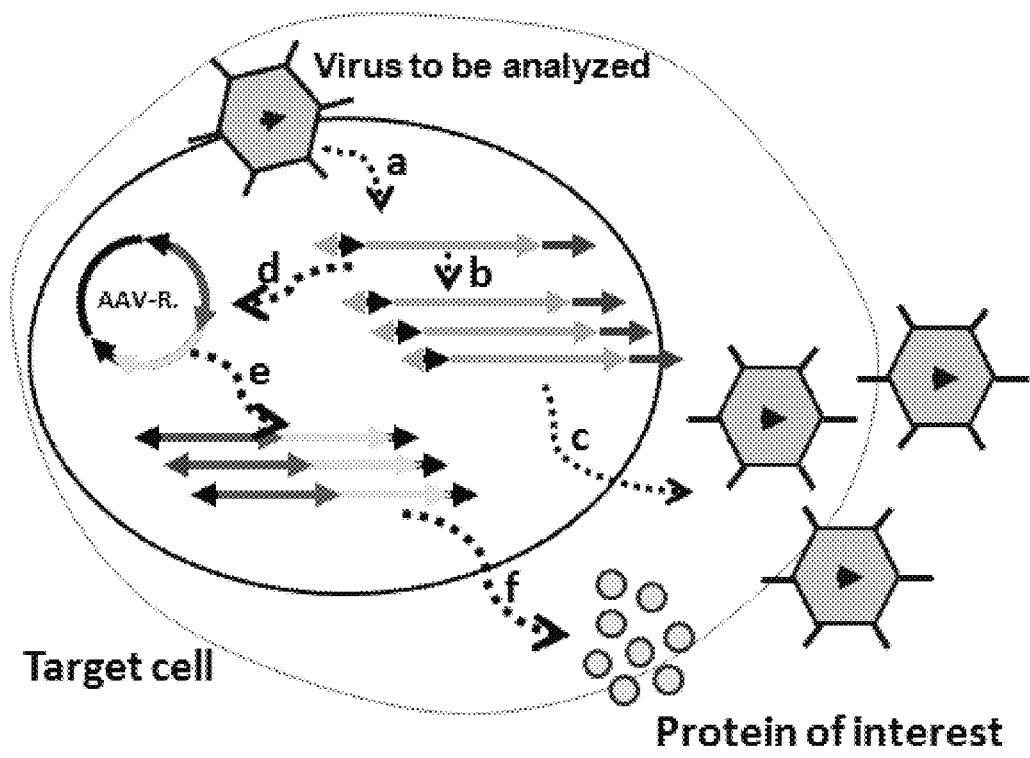
Figure 1E:
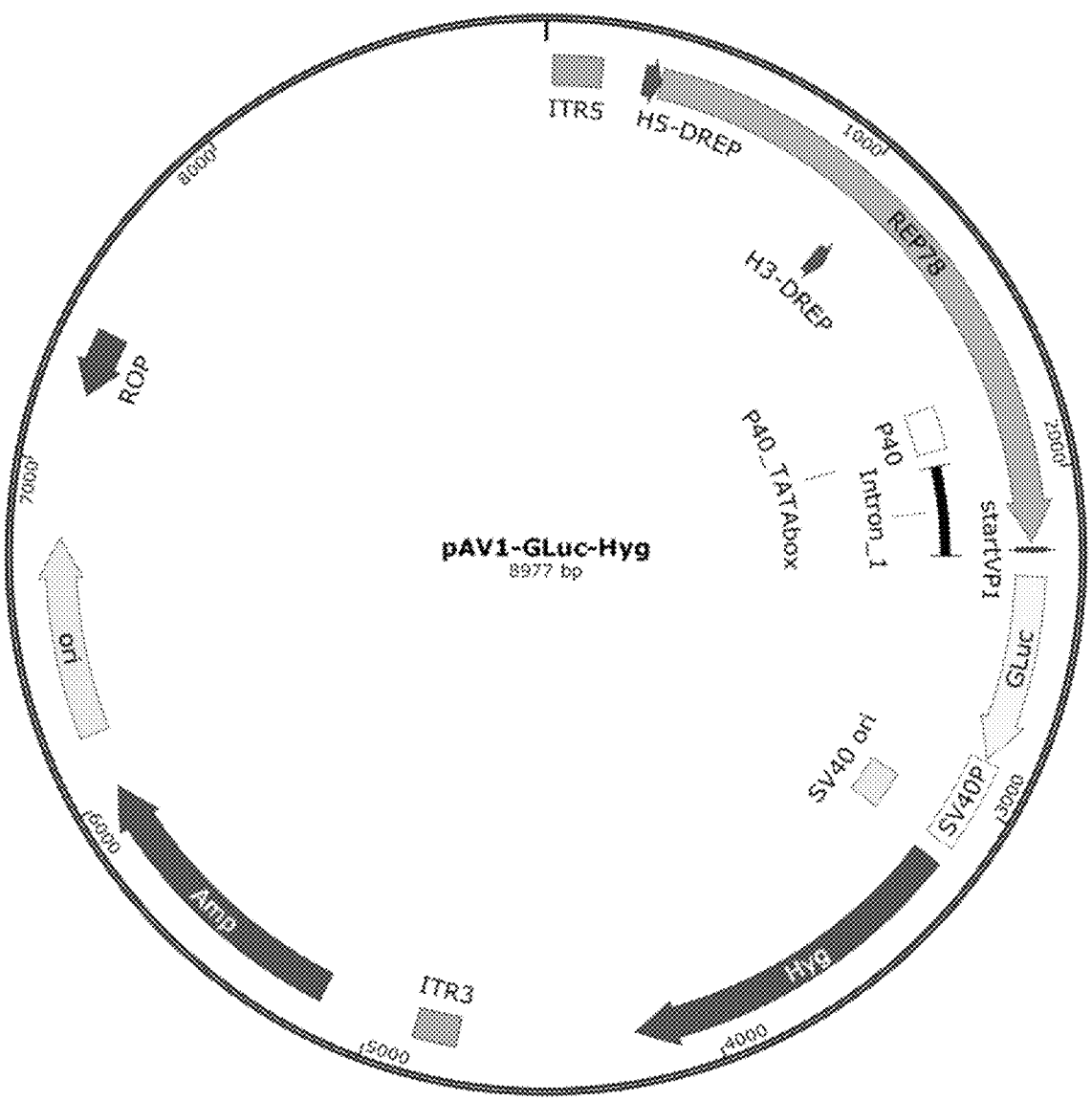

The figures show:

FIG. 1
- A) FIG. 1A: Schematic representation of a replicon of the invention. ITRs, inverted terminal repeats=AAV ori; REP, rep genes=non-structural proteins of AAV; GLuc, gaussia luciferase ORF; HYG, Hygromycin expression cassette; pBR332, bacterial vector).
- B) FIG. 1B: Experimental setting of the AAV based replicon vector for the analysis. To test the AAV based replicon, a target cell is transfected with the AAV replicon vector (AAV-R). These cells were then infected with a virus to be analyzed (e.g. a replication-competent Adenovirus (Ad)). After onset of Adenovirus DNA replication, the Ad genome amplifies. Concomitantly, and with expression of Adenovirus proteins and RNAs (together adenovirus helper functions), the AAV replicon vector is replicated and amplified. Then expression of the replicon-encoded gene of interest is induced and, after secretion, the protein can be detected in the cell culture supernatant.
- C) FIG. 1C: Sequence of a preferred replicon vector of the invention.
- D) FIG. 1D: Sequences of preferred rep proteins.
- E) FIG. 1E: Schematic representation of a replicon of the invention with further annotations.

Figure 2A:
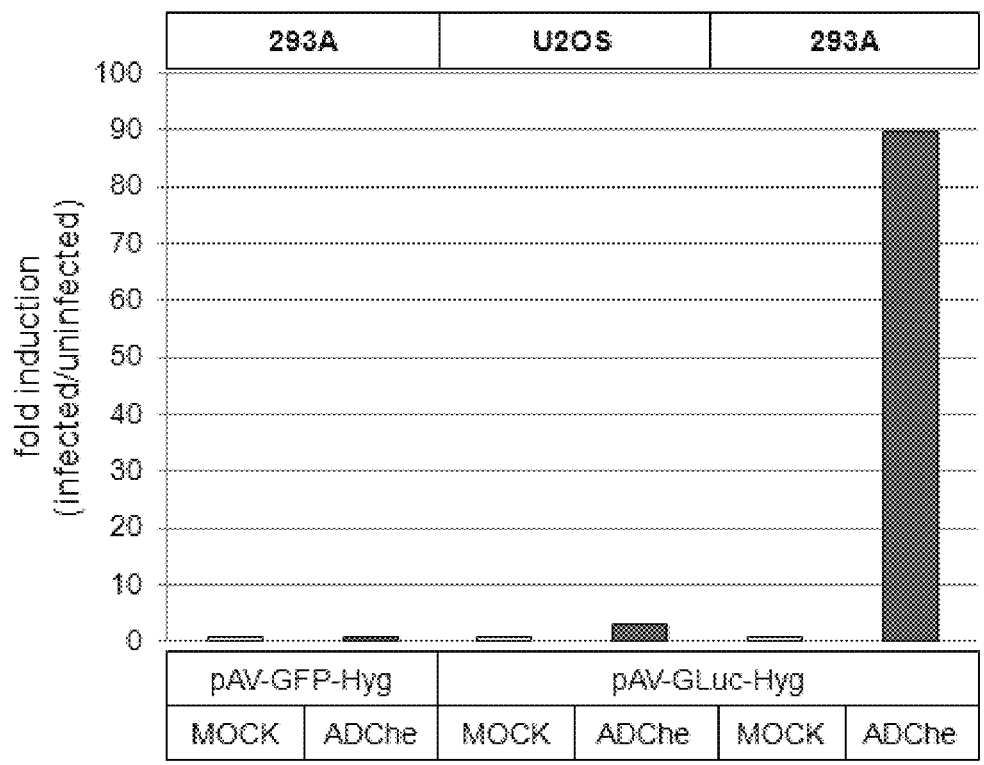
Figure 2B:
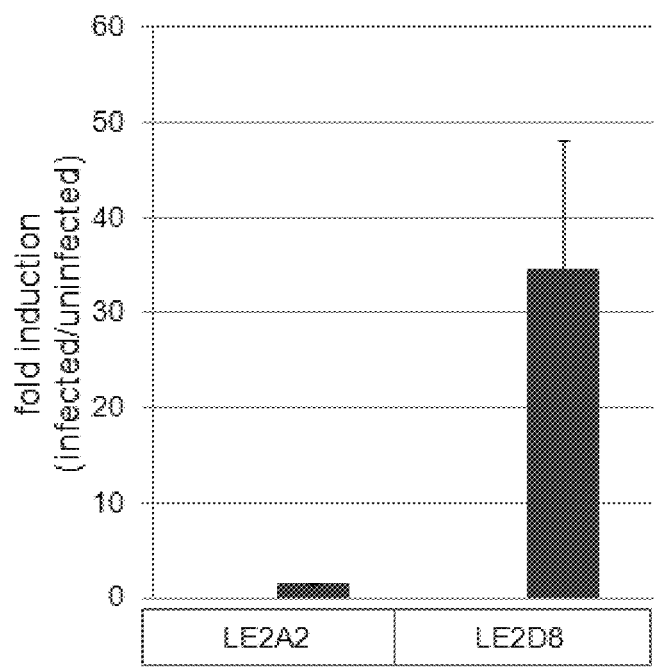

FIG. 2
- A) FIG. 2A: Adenovirus induced replicon response upon transient transfection. 293A and U2OS cells were transfected with pAV-GLuc-Hyg (GLuc) or pAV-GFP-Hyg (GFP) and infected with AD5 expressing the m-Cherry protein (ADChe) at an MOI of 100 or mock-treated (MOCK). 24 h post-transduction, luciferase activity was measured and the values were compared to the respective mock infected cells. Representative of three experiments. Depicted are mean and SD of technical triplicates.
- B) FIG. 2B: Induction of replicon response of a stable cell line after Adenovirus infection. AAV replicon negative LE2A2 and positive LE2D8 cell lines were infected with ADChe at an MOI of 100 and induction of luciferase was measured 72 hpi. Measured luciferase activity values were compared to the respective mock infected cells. Representative of four experiments. Depicted are mean and SD of technical triplicates.

Figure 3A:
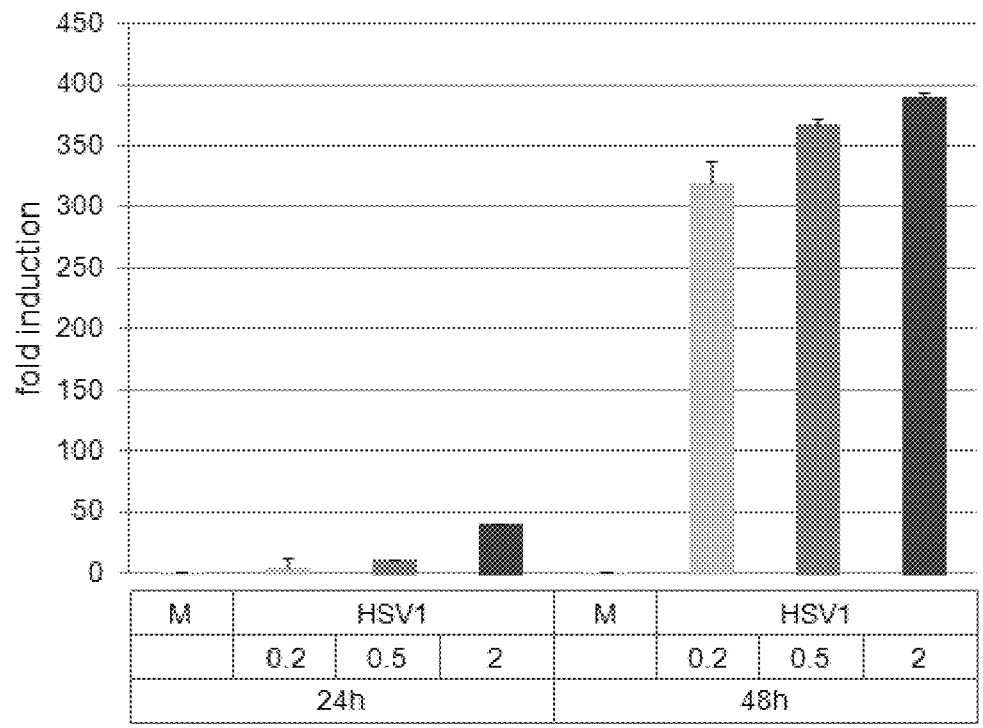
Figure 3B:
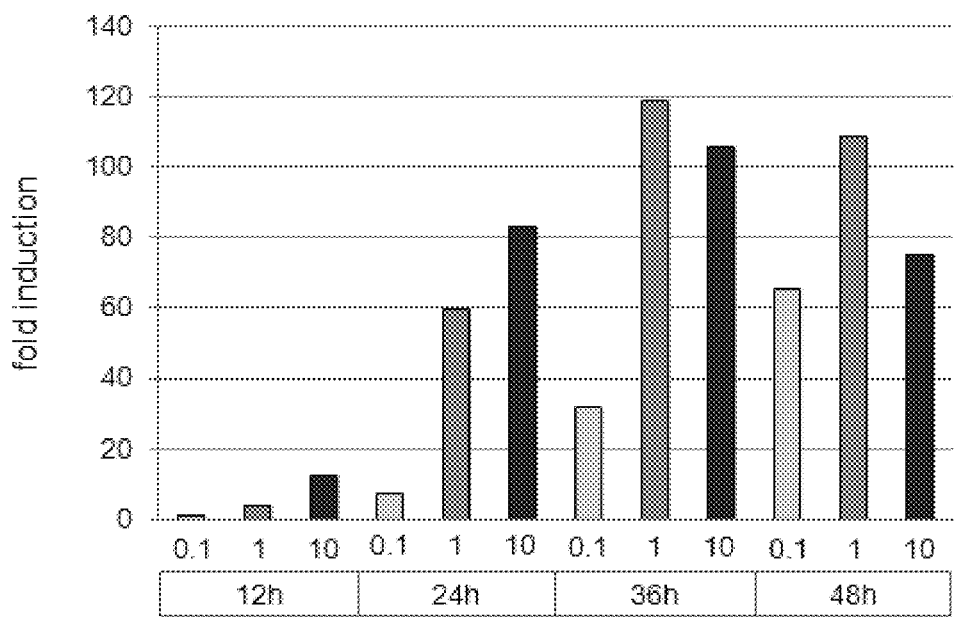

FIG. 3
- A) FIG. 3A: HSV-1 infection induced luciferase expression from the AAV replicon. 293A cells were transfected with the AAV replicon vector. Cells were infected with HSV1 at an MOI of 0.2, 0.5 and 2 72 h after transfection and luciferase activity in the supernatants were measured 24 and 48 hpi. Values were compared to the MOCK-infected cells. Depicted are mean and SD of technical triplicates.
- B) FIG. 3B: Luciferase expression after infection of replicon containing stable cell line with HSV1. The cell line LE2D8 was infected with HSV1 at an MOI of 0.1, 1 and 10. Luciferase activity in the supernatants was measured 12, 24, 36 and 48 hpi. Values were compared to the MOCK-infected cells. Depicted are mean and SD of technical triplicates.

Figure 4A:
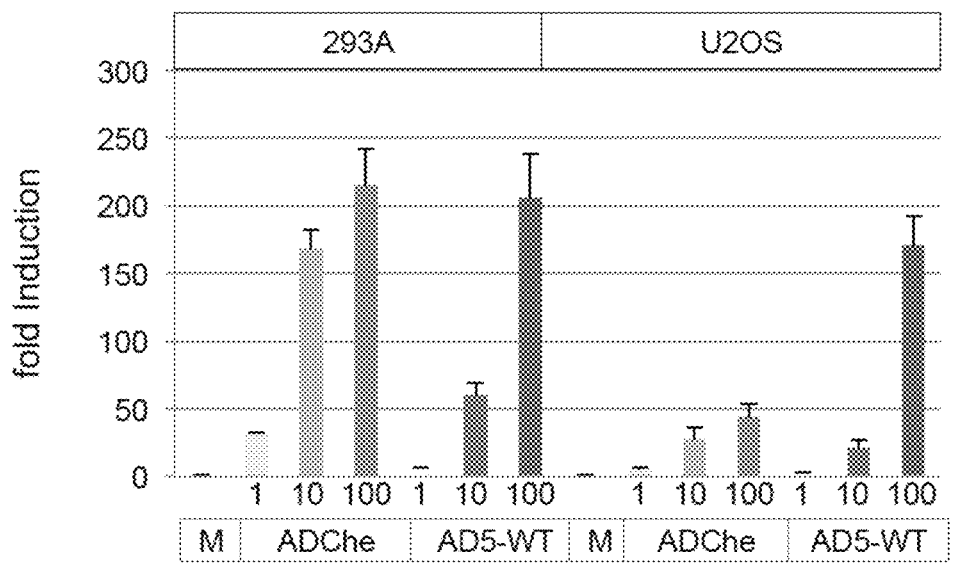
Figure 4B:
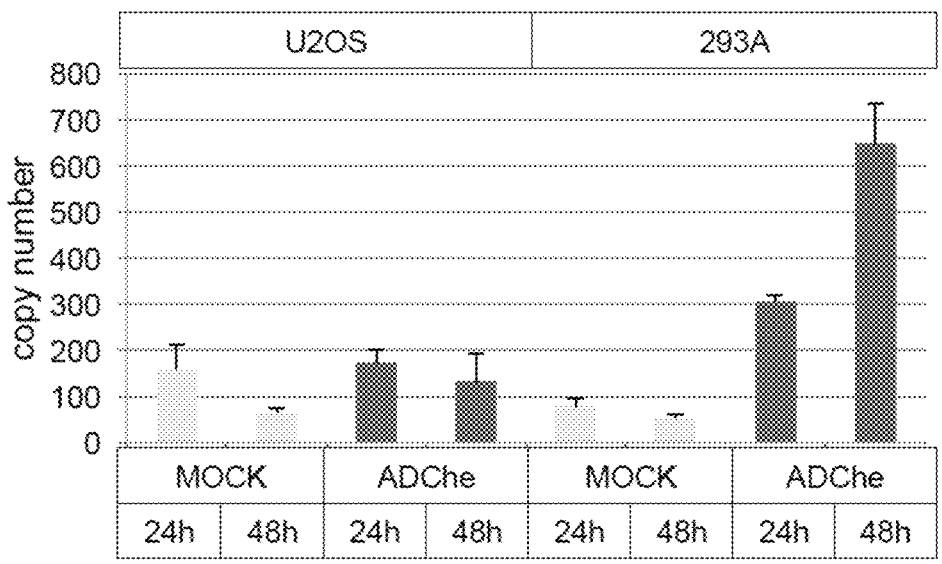
Figure 4C:
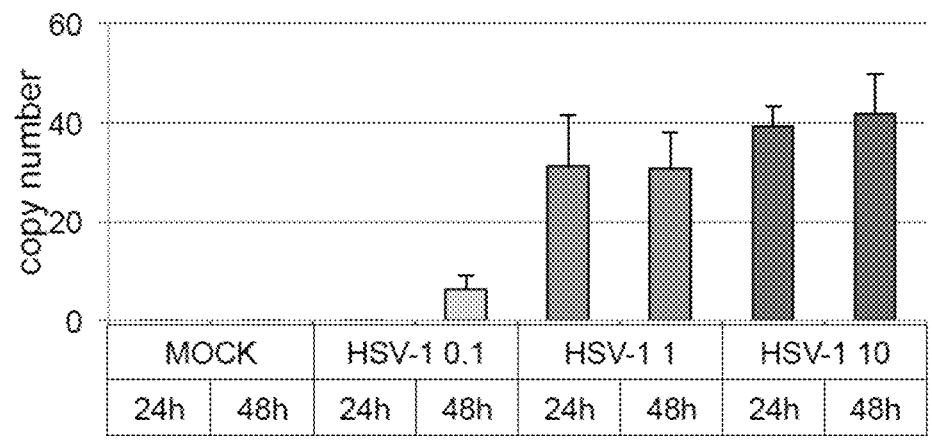

FIG. 4
- A) FIG. 4A: Optimal induction of the AAV replicon requires productive helper virus infection. 293A and U2OS cells were transfected with the AAV replicon vector pAV-GLuc-Hyg and infected with first generation human Adenovirus type 5 vector expressing mCherry (ADChe) or wild type human adenovirus type 5 (AD5-WT) 3 dpt with MOIs of 1, 10 and 100, respectively. Measurement of luciferase activity in the supernatants at 2 dpi was compared to the MOCK infected cells. Depicted are mean and SD of technical triplicates of one representative data set.
- B) FIG. 4B: Amplification of the replicon vector upon AD5 infection. Genomic and viral DNA was purified from 293A and U2OS transfected with the AAV replicon vector and transduced with ADChe. Copy number of GLuc per haploid genome was determined by relative real-time PCR. Amplification of the housekeeping gene GADPH was utilized to quantify the haploid genome number of 293A and U2OS cell line. Depicted are mean and SD of duplicate samples.
- C) FIG. 4C: Amplification of the AAV replicon vector in LE2D8 cells upon HSV1 infection. Genomic and viral DNA was purified from LE2D8 cell line infected with HSV1 at MOI of 0.1, 1 and 10 after 24 and 48 hours. Copy number of GLuc per haploid genome was determined by semi-quantitative real-time PCR. Amplification of the cellular housekeeping gene GAPDH was utilized to quantify the haploid genome number of the cell line. Depicted are mean and SD of duplicate samples.

Figure 5A:
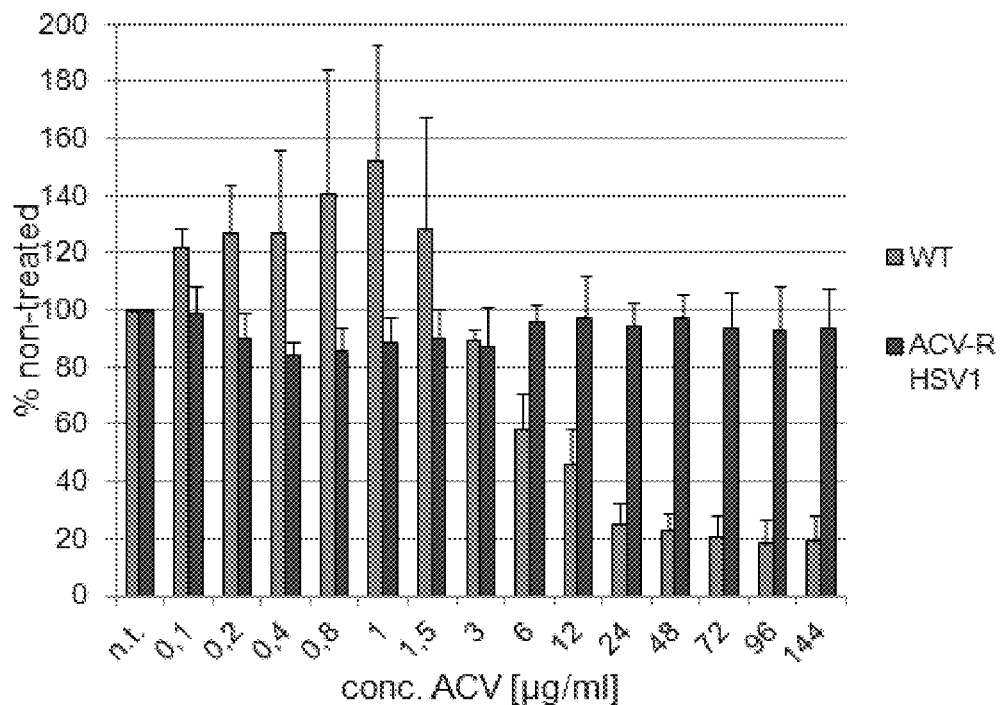
Figure 5B:
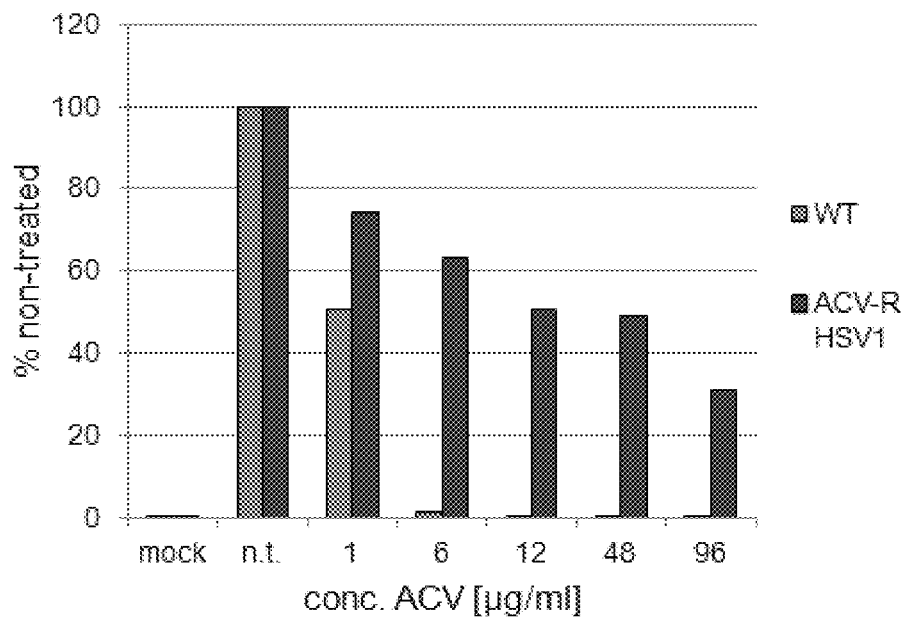

FIG. 5
- A) FIG. 5A: Infection of ACV treated LE2D8 cells with ACV sensitive and ACV resistant HSV1 strains. LE2D8 cell line were treated with different concentrations of ACV ranging from 0.05 to 144 µg/ml following an infection with either wild type HSV-1 or ACV resistant HSV-1 at an MOI of 0.035. 48 hpi GLuc activity was evaluated and compared to infected but non-treated cells. Representative of three experiments. Depicted are mean and SD of technical triplicates.
- B) FIG. 5B: Validation of resistance test of ACV sensitive- and ACV resistant HSV1 strains by endpoint dilution assay. LE2D8 cell line was treated with different concentrations of ACV ranging from 1 to 96 µg/ml following an infection with either wild type HSV1 or ACV resistant HSV1 at an MOI of 0.035. Infections were counted at 7 dpi and TCID50 values were calculated. Depicted are mean and SD of technical duplicates.

Figure 6A:
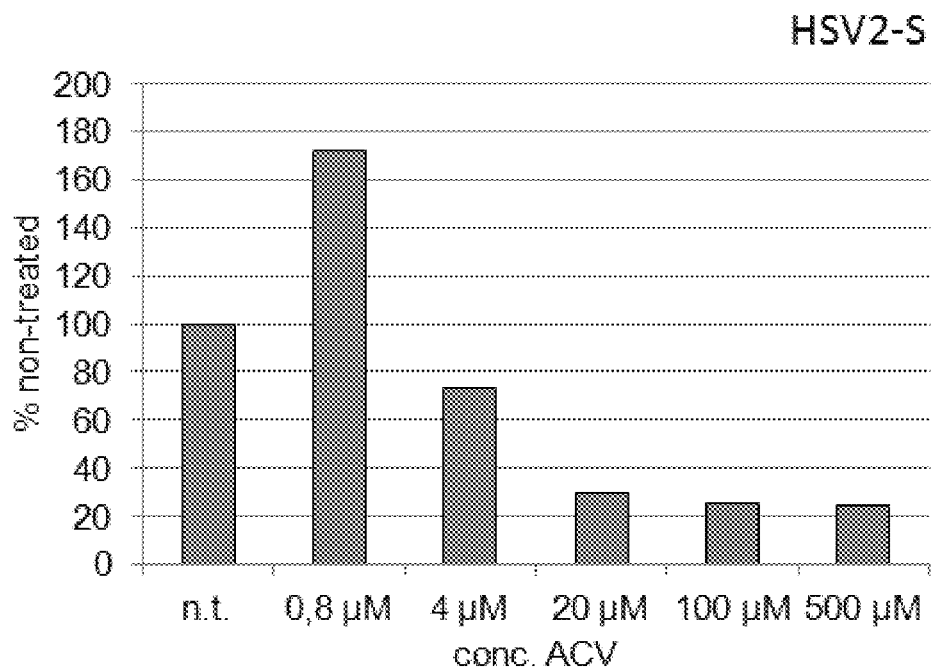
Figure 6B:
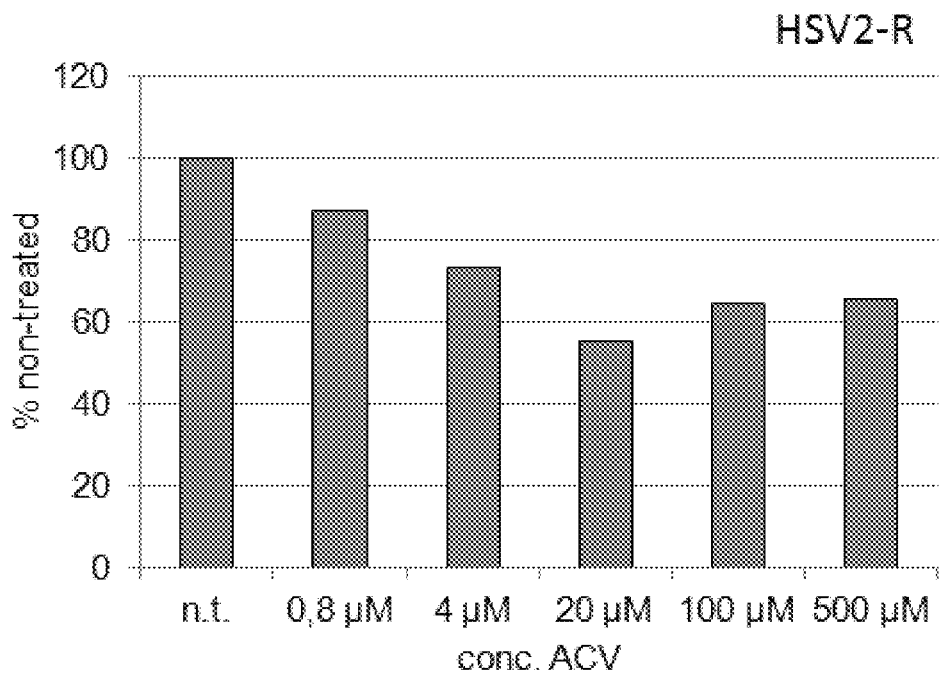

FIG. 6
FIGS. 6A-6B: Applicability of AAV replicon based resistance test with clinical HSV2 isolates. LE2D8 cell line was treated with different concentrations of ACV (0.8, 4, 20, 100 and 500 µM) following an infection with a sensitive HSV2 strain (FIG. 6A) or an ACV resistant HSV2 strain (FIG. 6B) at an MOI of 0.035. 48 hpi GLuc activity was evaluated. Depicted are mean and SD of technical triplicates.

FIG. 7

FIG. 7: Human adenoviruses from different species induced replicon response. 293A cells were transfected with pAV-GLuc-Hyg and infected with Ad5 expressing the m-Cherry protein (ADChe) as a control and several different serotypes: Ad12 (species A, A12), Ad3 and Ad11 (species B, B3 and B11), Ad9 and Ad17 (species D, D9 and D17), Ad4 (species E, E4) at an MOI of 1. 24 h post-infection, luciferase activity was measured and the values were compared to the luciferase activity of mock infected cells. Depicted are the means of relative induction values (fold induction) and SD of technical triplicates.

FIG. 8

FIGS. 8A-8B: Freezing and pre-seeding of already transfected cells allows AAV replicon induction by HSV-1 infection. 293A cells were transfected with pAV-GLuc-Hyg, frozen and pre-seeded onto a 96 well plate after (FIG. 8A) 24 hours and (FIG. 8B) 48 hours after transfection. The transfected cells were thawed and 4, 6, 20 and 26 hours after thawing infected with HSV-1 at an MOI of 0.01, 0.1 and 1. At 48 hpi GLuc activity was measured. Depicted are the ratios of luciferase activities between infected and mock infected cells (fold induction); mean and SD of technical triplicates are shown.

FIG. 9

FIGS. 9A-9C: Inducibility of the AAV replicon system transduction. FIG. 9A: A549 cells were transduced with rAAV Replicon particles at indicated densities (pt/cell) and infected with Ad5 at MOI 10, 6 hpt (hours post transduced) or kept MOCK infected. 48 hpi GLuc activity was measured and compared to the luminescence of transduced but non-infected cells. Values represent the average of three experiments. FIG. 9B: Vero cells were transduced with rAAV and after 6 hpt infected with either HSV-1 or HSV-2 at MOI 0.1. Results of luciferase activity measurement in the supernatants at 24 hpi and 48 hpi were compared to MOCK infected transduced cells. Values represent the average of three experiments. FIG. 9C: rAAV Replicon particles transduced HFF cells were infected with HCMV at MOI 1, 6 hpt and Sp was collected after 4 and 7 days p.i. Luciferese activity was measured and the values were compared to the luciferase activity of MOCK infected transduced cells. Values represent the average of one experiment. Error bars show the standard deviations from the mean of technical triplicates.

The examples illustrate the invention:

EXAMPLE 1

Exemplary Replicon Vector

To test the characteristics of the AAV replicon system we constructed an AAV replicon vector which carried a luciferase ORF as marker gene. This allowed us to test the inducibility of the AAV replicon in different experimental setting. We used the pAV1 plasmid (ATCC #VR37215) as a source for AAV sequences. We replaced the AAV between the unique recognition sites for the XhoI and ApaI by a synthetic oligonucleotide sequence encompassing a multiple cloning site and the hygromycin resistance cassette derived from pTRE-Hyg (invitrogen). The XhoI site is located 380 nt downstream of the p40 transcription initiation site at the very beginning of the AAV VP1 ORF, and the ApaI site is located in the front of the right ITR (486 nt upstream) at the end of the cap coding sequence. Into this intermediate we inserted a PCR amplified luciferase ORF from pGLuc (NEB). This construct was termed pAV1-GLuc-Hyg (FIGS. 1A and 1C and SEQ ID NO: 1). For control reasons we also inserted the ORF of the green fluorescent protein (GFP) into the same position of amplifying the ORF present in pEGFP-N1 (Clontech). This control construct was termed pAV1-GFP-Hyg.

The experimental setting to investigate the inducible gene expression system based on the AAV replicon in this study possessed three components: the target cells, the AAV replicon construct with the expression cassette for the gene of interest, and the virus of interest. The replicon vector was first introduced into the target cells and then the replicon carrying target cells were infected with the virus of interest. If the infecting virus can induce AAV replication (is an AAV helper virus) the replication cycle of the virus will proceed in the target cells. The products of the lytic cycle of the helper virus will induce the replication of the AAV replicon vector and activate the expression of the gene of interest. The transgene expression was analyzed after different time point after infection and compared to the gene expression of the non-infected replicon carrying target cells.

EXAMPLE 2

Providing the Target Cells by the AAV Based Replicon System: Transient and Stable Transfectants We tested the inducible expression of the AAV replicon vectors using two different transfection protocols. First we transiently transfected different cell types with the AAV replicon vectors carrying the reporter genes. This approach allowed us to test our system in different cell lines. The advantage of using a transient transfection protocol in different cells is the applicability of the AAV replicon technology to helper viruses which replicate in specific cell lines. The disadvantage of this method is that the transfection protocol prolongs the assay time and due to the different transfection efficiencies between the experiments, normalization of the gene expression data is required by an additional housekeeping marker. Therefore, we also generated a stable cell line based on 293A cells, carrying an integrated copy of the AAV replicon. To generate a stable cell line, the human 293A cells (Invitrogen) were transfected with pAV1-GLuc-Hyg and selected for hygromycin resistance. The stable clones were isolated by limiting dilution method in continuous presence of hygromycin. After testing a set of resulting clone we selected a replicon negative (LE2A2) and a replicon positive stable clone (LE2D8) and expanded them with serial passages. These 293A based cell lines were then used in the following experiments testing the AAV replicon technology in the context of stable transfection. This approach provided shorter testing times and assay to assay reproducibility. The disadvantage of this technology is that the gene expression levels are expected to be lower than those obtained using the transient system.

EXAMPLE 3

Induction of the Replicon System Using Different Viruses 3.1 Adenovirus Induction To test whether the AAV replicon vector responds to its most commonly used helper virus we first tested the replicon response to adenovirus (Ad) infections. To this end, we transfected U2OS and 293A cells with 1 µg Litmus28 as a placeholder DNA, 0.5 µg pO6-CMVmChe, which constitutively expresses mCherry as housekeeping marker, and 0.5 µg of the specific constructs following the transfection protocol of SuperFect Transfection reagent (Qiagen). The specific constructs were the luciferase expressing AAV replicon (pAV-GLuc-Hyg) and a control replicon vector carrying a GFP expression cassette (pAV-GFP-Hyg). 48 h after transfection the transfected cells were seeded to 96-well plates at density $3.3 \times 10^4$ per/well. Then we infected the cells, always using technical triplicates, with a recombinant adenovirus type 5 expressing mCherry (ADChe) at an MOI (multiplicity of infection) of 100. This E1 and E3 deleted first generation AD5 vector expressing an mCherry marker was used as a model of complementation-dependent adenovirus. Since the 293A cells are able to trans-complement the E1 gene, which is missing in this defective virus, these cells support a productive virus cycle of such Ads. However, U2OS cells cannot complement the genetic deficiency of first generation Ad vectors. Therefore, in these cells only virus entry and expression of some early genes will take place, but DNA replication and productive infection cannot proceed.

To analyze the expression of the luciferase gene expression, we used the BioLux® Gaussia Luciferase Flex Assay Kit measuring the luciferase activity of 20 µl cell culture supernatants transferred directly from the assayed wells of the infected 96 well plates. The luminometer was adjusted with the following parameters: injection of 50 µl GLuc assay solution, 2 s shaking, 35-40 s delay and 10 s of integration. The primary luminescence was recorded for each sample and these values were compared to the primary luminescence of transfected but non-infected cells. Each measurement was done once for each technical triplicate and the data are depicted in FIG. 2A. As expected, the control cells, which were transfected with the GFP expressing replicon vector, showed no difference in light emission after infection, because they did not express luciferase. A moderate increase of the luciferase signal was observed in pAV1-GLuc-Hyg transfected U2OS cells, indicating that an abortive Ad infection was able to induce some AAV replicon derived luciferase expression. In 293A cells, however, the luciferase expression was increased by about 100 fold, indicating that a productive adenovirus infection was able to strongly induce the AAV replicon based gene expression.

To test whether the AAV based replicon can be induced by Ad infection in the context of stable cell line we infected LE2A2 and LE2D8 cell lines with ADChe at MOI of 100. As shown in FIG. 2B the replicon negative LE2A2 cell did not responded to Ad Infection but in the replicon positive LE2D8 cells responded to Ad infection with more than 30 fold increase of luciferase expression to Ad infection.

3.2 Induction of the AAV Based Replicon Vector by Herpes Simplex Virus Infection Since AAV can also be reactivated by herpesvirus coinfection, we tested the response of the AAV replicon vector to HSV-1 infection. To this end, 293A cells were transfected with pAV1-GLuc-Hyg as described before (2.1), and infected at 3 day after transfection (dpt) with HSV1 at MOIs of 0.2, 0.5 and 2. The HSV1 strain used in this experiment was a BAC derived herpes simplex virus type 1 (HSV1) laboratory strain (Nagel et al. J Virol., 82:3109-3124 (2008)). Luciferase activity in the supernatant was measured 24 and 48 h after infection (hpi) and compared to the mock-infected cells (FIG. 3A).

One day after infection with HSV1, induction of luciferase expression from the AAV replicon was detectable on all samples, yielding the highest value (~50-fold) for cells infected at an MOI of 2. On day 2 post-infection, luciferase activity was even higher, with values ranging between 320-fold (MOI 0.2) and 390-fold (MOI 2) induction. These values were the highest induction we measured in the course of this study.

To test, if the replicon induction with HSV1 is as well present when the AAV replicon is provided by the stable system, we infected the cell line LE2D8 with HSV1 at different MOIs of 0.1, 1 and 10 and harvested the supernatants after 12, 24, 38 and 48 hours. Luciferase expression was evaluated and values were compared to mock infected cells (FIG. 3B).

A 12-fold induction of luciferase expression was detected already at 12 hpi and at an MOI of 10. A virus load dependent increase of luciferase induction was evident at 24 hpi. The maximum induction was received after only 36 hpi at an MOI of 1 with a value of 120-fold induction.

To our surprise, we could conclude that HSV1 was the strongest inducer of the AAV replicon vector both in the context of the transient and the stable system.

3.3 Replicon Replication is involved in the Mechanism of the Induction of the Gene Expression Next we wanted to test whether the productive helpervirus replication is needed for the optimal AAV replicon response. To this end, 293A and U2OS cells were transfected using 1.25 µg Litmus28, 0.5 Ng of the specific DNA (pAV-GLuc-Hyg) and 0.25 µg housekeeping marker using SuperFect as transfection reagent. The last plasmid is an expression vector for firefly luciferase. We introduced it into the assay as transfection control (instead of the mCherry expression plasmid used in the experiments above) in order to allow quantitative normalization between the experiments using luminometry. Cells were infected with ADChe vector and wild type (wt) Ad type 5 (AD5-WT) 3 dpt at MOIs of 1, 10 and 100. The supernatants were collected 48 h later and luciferase activity was measured as indicated above. The entire experiment was repeated 3 times and the ADChe inductions 6 times.

As shown in FIG. 4A, a clear increase of luciferase expression was observed after infection of replicon transfected 293A cells with increasing doses of ADChe. The same was true for infection with wt AD5 in 293A cells. However, in U2OS cells a similar increase was observed only for wt AD5 infection. After infection with ADChe only a moderate induction was observed, which was still dose dependent. Since ADChe cannot replicate in U2OS cells lacking the E1 genes, but wt AD5 replicates well, these data indicated that the AAV replicon response consists of two components. One which can be observed in any cells, most likely based on transactivation of the AAV promoters by a sub-set of Ad early genes. The second, more pronounced effect seemed to depend on productive Ad infection.

To confirm that productive Ad infection indeed induced the AAV replicon mechanism including replicon vector amplification, we set up a semi-quantitive real-time PCR to directly measure the change in the copy number of the transiently transfected pAV-GLuc-Hyg replicon vector upon Ad infection.

Three days after transfection, 2 wells of transfected cells were seeded onto a 12-well-plate and infected with ADChe at an MOI of 100 or mock treated. Cells were harvested after 1 and 2 days and cellular DNA was purified using the DNeasy® Blood & Tissue Kit according to the manufacturer's instructions. In order to analyze the replication efficiency of the target sequence. GLuc quantitative PCR was performed by the Lightcycler system using SYBR® Green PCR Kit. Real-time PCR reaction was performed using duplicates of the samples. The thermal cycling conditions were 15 min at 95° C., 45 amplification cycles of 15 s at 95°

C. (denaturation), 30 s at 58° C. (annealing) and 30 s at 70° C. (elongation). Melting curve analysis followed with 15 s at 65° C. and at the end there was a cooling down phase to 37° C.

We used the primers GLucfor (GTGTAGGCCTCG-GATCCAGCCACCATGGGAGTC; SEQ ID NO: 2) and GLucrev (CCATAGAGCCCACCGCATCCCC; SEQ ID NO: 3) to amplify the GLuc gene and primers GADPH for (TGGTATCGTGGAAGGACTCA; SEQ ID NO: 4) and GAPDHrev (CCAGTAGAGGCAGGGATGAT; SEQ ID NO: 5) to amplify the human housekeeping gene of Glyceraldehyde-3-phosphate dehydrogenase (GAPDH), which is present in one copy for each haploid genome in human cells. The copy numbers per haploid genomes (copy number/HG/) were determined at the point where doublings reached linear phase (CT) according to the equation:

copy number/HG/=$2^{(CTh-CTI)}$. Where HG is the housekeeping gene, CTh is the CT value for the housekeeping gene and the CTI is the CT value for the GLuc amplification. Primary copy numbers for the GLuc-specific amplification were calculated using CT values of each amplification curve and normalized against the copy numbers of GAPDH. This allowed relative quantification of the GLuc copy numbers for both days (FIG. 4B).

Between 55 and 78 GLuc copies were detected in mock-infected 293A cells, originating from maintenance of the transfected replicon vector DNA. On day 1 after ADChe infection, approximately 300 replicon genomes per haploid host genome were detected in 293A cells, which increased up to 650 copy numbers on day 2. These data confirmed that in 293A cells the productive virus infection indeed induced the replication of the AAV replicon vector. In contrast, in U2OS cells where ADChe cannot replicate, the copy number of the replicon vector per haploid genome decreased from day 1 to day 2 (170 to 130 copy) as in mock-treated (160 to 65 copy). This decrease in the relative copy numbers on the second day can be explained by an increase of the cellular genome copies by cell division during the assay time.

To test the replication of the AAV replicon vector in the context of stable transfection, we infected LE2D8 cells with HSV1 laboratory strain in 12-well-plates. The changes of the AAV replicon copy numbers were measured as above.

The LE2D8 cell line was infected with HSV-1 at MOI of 0.1, 1 and 10 or mock treated. Total DNA was purified either after 24 and 48 hours after infection. Then a real-time PCR was performed, amplifying the cellular housekeeping gene GAPDH and the transgene coding sequence GLuc. CT values, calculated from primary copy numbers of GLuc specific amplification, were normalized against the CT values of GAPDH.

The quantification of the GLuc copy numbers for both days showed clearly the dependence of the GLuc copy numbers on the viral load. In mock infected and cell infected at an MOI of 0.1 the GLuc copy number were around detection limit at day 1. However, at MOI of 0.1 the on day 2 6 GLuc copy was detectable per haploid genomes. In cells infected with HSV1 at MOI of 1, ~30 GLuc copies were detectable on both days; at MOI of 10 a further moderate increase of GLuc copies were evident (39 and 42 copy numbers on day 1 and day 2) as well (FIG. 4C). These data showed that the replication of the replicon vectors was indeed induced by helper virus infection in both the transient and stable transfection settings.

EXAMPLE 4

The AAV Based Replicon Technology can be Used to Test Drug Sensitivity of Clinical Virus Isolates Considering the fact, that the replicon positive cell line LE2D8 responds to HSV1 replication, we built up an assay to differentiate drug sensitive and drug resistant clinical isolates. Aciclovir (ACV) is the most prominent drug used for treatment of human HSV1 infections. It is a guanosine analogue and inhibits the viral DNA polymerase and consequently ACV inhibits HSV1 replication. If the AAV replicon response is dependent on the HSV1 replication the system should respond differently in the presence of ACV to infections with an ACV-sensitive HSV1 strain (which cannot replicate in this condition) and to an infection with an ACV resistant strain (which can replicate in this condition).

The cell line LE2D8 was seeded onto 96-well-plates at density of $3.3 \times 10^4$ cell/well. Two hours after seeding the cells were left untreated or were treated with different concentrations of ACV (CAS: 59277-89-3) (ranging from 0.05 to 144 µg/ml). Right after treatment the cells were infected with either a wild type ACV sensitive HSV-1 laboratory strain or an ACV resistant strain (kindly provided from Dr. Gundula Jäger, Max von Pettenkofer-Institute, LMU Munich) using an MOI of 0.035. After only 48 hpi luciferase activity in 20 µl of the supernatant was measured as the previous experiments. The luciferase activities of the ACV treated cells were compared to the luciferase activities obtained after infection of the non-treated cells. The luciferase induction of the non-treated cells was set 100% and the activity of the ACV treated cells was depicted as % of the non-treated values (FIG. 5A).

For the laboratory strain already at an ACV concentration of 6-12 µg/mi a strong inhibitory effect could be observed decreasing the luciferase activity to 20% of non-treated cells. In contrast the resistant HSV1 strain induced the AAV replicon derived luciferase expression similar to the non-treated control indicating that ACV treatment could not inhibit the virus replication.

For the validation of the new established replicon based assay we made an endpoint-dilution-assay to monitor the amount of the produced viruses in presence of the ACV treatment. This standardised assay for detection of viral growth is very sensitive but very time consuming since 5-7 days are required to obtain the results. To test the virus production in our assay condition with the standard method the sensitive and ACV-resistant HSV-1 containing assay supernatants of the infected LE2D8 cells treated with different concentrations of ACV (n.t., 1, 6, 12, 48 and 96 µg/ml) were collected. Subsequently endpoint dilution assays were performed using HEK-cells in a 96 well plate format. The Tissue Culture Infection Dose 50 (TCID50) was calculated after collecting the infectivity counts at day 7 (FIG. 5B). These data confirmed that the virus replication of ACV sensitive laboratory strain was indeed inhibited by ACV treatment and ACV could not inhibit the replication of a resistant HSV1 strain on the LE2D8 cells in the assay conditions.

As a next step we analysed the usability of the AAV replicon based resistance test for HSV2 clinical isolates. We tested different known and unknown HSV-2 isolates in cooperation with the clinical diagnostic of the Universitätsklinikum Freiburg, in Freiburg.

For testing the single HSV-2 virus isolates, LE2D8 were seeded to $3.3 \times 10^4$ cells in a 96 well format, 2 hours before treatment with 0.8, 4, 20, 100 and 500 µM ACV and infection with 1:10 diluted HSV-2 isolates, always using technical triplicates. After 48 hpi, GLuc activity in the supernatant was measured by luminometry and values were compared to non-treated and mock infected cells as above. In FIGS. 6A and 6B we show example of the replicon response induced by an ACV sensitive HSV2- and one of an ACV resistant HSV-2 isolate.

The AAV replicon based resistance test was able to distinguish between ACV sensitive and resitant HSV-2 viruses isolates derived from HSV infected patients. In FIG. 6A the result shows the typical pattern of a sensitive strain, by decreasing amounts of GLuc activity upon treatment with 20 μM and higher concentrations of ACV compared to non-treated cells. In contrast, the luciferase induction pattern of the resistant HSV-2 strain is different. For the ACV concentrations tested, the GLuc induction never decreased below 50% of the non-treated values.

Induction of the AAV Based Replicon Vector by Different Ads

Mastadenoviruses including human adenoviruses are divided into six species (species A-F) according to their genetic and biological features. AAV replicon system was proven to be induced well by recombinant and wild type human adenovirus type 5 (Ad5), a species C adenovirus. Since in clinical praxis adenoviruses isolates are frequently found from other species than C (mainly species B and D), we tested whether different human adenoviruses representing other species are able to induce a comparable replicon response what we observed for Ad5. To this end, 293A cells were transfected with pAV1-GLuc-Hyg following the transfection protocol of FuGene HD Transfection reagent (Promega), and infection followed 3 day after transfection. The cells were seeded on 96-well-plates at the density of $3.3\times10^4$ cells/well and infected with the following human adenovirus serotypes: Ad12 (species A), Ad3 and Ad11 (species B), Ad9 and Ad17 (species D), Ad4 (species E), at MOI of 1. As a control the recombinant adenovirus type 5 (ADChe) infection was used at MOI of 1. Luciferase activity in the supernatant was measured 48 h after infection (hpi) and compared to corresponding mock-infected cells (FIG. 7). Induction of AAV-replicon derived luciferase expression could be observed upon infection with all adenovirus serotypes, yielding values between 16 and 58-fold induction comparable for the induction with ADChe (20 fold). These data indicates that the AAV-replicon response can be induced well with a wild range of human adenoviruses derived from different species.

EXAMPLE 5

Induction of the AAV Replicon by Infection Using Frozen Transfected Cells

The AAV replicon may be introduced by transient transfection or stable cell lines may be used. The assay may take 3 days longer if transient tranfection is applied because it is necessary to wait between transfection and infection in order to let the cells recover after transfection. To save this 72 h assay time in transient transfection we transfected 2E+05 293A cells in 6 well with 0.6 μg pAV1-GLuc-Hyg and 5 μg Litmus 28 stuffer DNA using FuGene according to the manufacturer's protocol. 24 and 48 hours later the cells were re-suspended in freezing media (Dulbecco's Modified Eagle Medium (DMEM), 20% Fetal bovine serum (FBS) and 10% Dimethyl sulfoxide (DMSO)) and seeded onto 96-well-plates at a density of $3\times10^4$ cells/well: Plates were sealed and then rapidly frozen in −80° C. For thawing of the plates 150 μl of growth medium was added directly to each well and cells were incubated for 2 hours under normal cell culture conditions. Then, the supernatant was removed and 100 μl of growth medium was added to each well. 4, 6, 20 and 26 hours after thawing the pre-transfected 293A cells were infected with a HSV-1 laboratory strain using an MOI of 0.01, 0.1 and 1. After 48 hpi luciferase activity was measured in 20 μl of the supernatant as in previous experiments. The induction of the luciferase activity was calculated by comparing the values after HSV-1 infection to mock infected cells (FIG. 8).

Induction of the reporter gene by HSV-1 infection could be observed for either freezing the 96-well-plates 12 or 48 hours after transfection independent of the amount of virus particles. In general the induction was higher after infecting the plates, which were frozen 48 hours after transfection. Here infection with MOI of 0.01 showed a 8-fold luciferase induction compared to a 3-fold induction after freezing the plates 24 hours after transfection. The highest induction (58-fold) was obtained by freezing the plates 48 hours after transfection and infecting those 28 hours after thawing using an MOI of 1.

This data shows that freezing and pre-seeding of AAV-replicon transfected cells is possible without affecting their inducibility upon HSV-1 infection. The method described allows the configuration of a standardized product, which can be used in a fast way.

EXAMPLE 6

Induction of a Recombinant AAV2 Vector Containing the AAV Replicon Gene

Since we were interested to overcome limitations based on the low transfection efficiency in certain cell lines, we investigated the recombinant adeno-associated virus (rAAV) as a potential replicon vector transducing system. For this, we transfected 2.30E+08 HEK 293TN cells with the plasmid pDP2rs (Grimm, D., M. A. Kay and J. A. Klenschmidt (2003). "Helper virus-free, optically controllable, and two-plasmid-based production of adeno-associated virus vectors of serotypes 1 to 6." Molecular Therapy 7(6): 839-850) for AAV production and the construct of the invention termed pAV1-GLuc-Hyg using PEI (Polyscience, PEI "Max", MW 40,000) according to the manufacturer's protocol. After 48 h the transfected cells were lysed by three rounds of freeze-thawing. Released rAAV-Replicon particles were purified and concentrated by iodixanol density centrifugation (Zolotukhin, S., B. J. Byrne, E. Mason, I. Zolotukhin, M. Potter, K. Chesnut, C. Summerford, R. J. Samulski and N. Muzyczka (1999). "Recombinant adeno-associated virus purification using novel methods improves infectious titer and yield." Gene Therapy 6(6): 973-985).

For testing the inducibility of the rAAV-Replicon transgene expression, the recombinant virus particles were transduced to A549, Vero cells and to the primary cell line HFF, using different amounts of rAAV-Replicon particles per cell (pt/cell) in a 96 well plate format. After 6 hours transduced cell lines were respectively infected with Ad5 at MOI 10, with HSV-1 and HSV-2 at MOI of 0.1 and with HCMV using MOI of 1 or kept mock infected. Subsequently the supernatants of transduced Ad infected cells were collected after 48 hpi, HSV-1 and HSV-2 infected cells after 24 and 48 hpi, and HCMV infected cells were collected after 4 and 7 days post infection. Luciferase activity was measured in 20 μl of the supernatant as in previous experiments. The induction of the luciferase activity was calculated by comparing the values after transduction and infection to transduced and mock infected cells (FIG. 9).

In summary there was no difference of luminescence between transduced and non-transduced cells indicating a tightly regulated system. All viruses tested could induce a replicon response in cells which were transduced with rAAV-replicon particles. In case of Ad5, HSV-1 and HSV-2 infection, increasing signal induction could be observed dependent on the amount of rAAV particles. After transduction of rAAV particles and Ad5 infection the highest fold induction (13.500 fold) of GLuc in the course of this study was measured. A similar increase of the replicon response could be observed for HSV-1, which showed at its maximum a 2800 fold increase. Furthermore, induction of GLuc of 215 fold in case of HSV-2 and 215 fold in case of HCMV confirms the usefulness of transducing the Replicon system via recombinant AAV particles.

What is claimed is:

1. A circular nucleic acid comprising in 5' to 3' direction
   (i) at least one adeno-associated virus (AAV) inverted terminal repeat (ITR) sequence;
   (ii) at least one AAV promoter which is capable of being activated by at least one helper polypeptide or helper polynucleotide originating or derived from a virus selected from Adenoviridae and Herpesviridae;
   (iii) at least one AAV rep gene coding sequence under the control of said promoter of (ii);
   (iv) an AAV promoter which is capable of being activated by said at least one helper polypeptide or helper polynucleotide originating from a virus selected from Adenoviridae and Herpesviridae;
   (v) a transgenic coding sequence under the control of said promoter of (iv); and (vi) an adeno-associated virus (AAV) inverted terminal repeat (ITR) sequence;
wherein said circular nucleic acid does not comprise an AAV cap gene.

2. The nucleic acid of claim 1, wherein
(a) the promoter of (ii) is one or more promoters selected from the group consisting of AAV promoters p5, p19 and p40; and
(b) the promoter of (iv) is selected from the group consisting of AAV promoters p40, p5, p19, and late promoters from a virus naturally encoding said helper polypeptide(s).

3. The nucleic acid of claim 1, wherein
(a) the promoter of (ii) is one or more promoters selected from the group consisting of AAV promoters p40, p5, and p19; and
(b) the promoter of (iv) is full-length p40.

4. The nucleic acid of claim 3, wherein the promoter of (ii) is the AAV promoter p5 in combination with the AAV promoter p19.

5. The nucleic acid of claim 1, wherein the at least one AAV rep gene coding sequence of (iii) encodes at least one of the AAV Rep78 or the AAV Rep68 polypeptide.

6. The nucleic acid of claim 5, wherein the at least one AAV rep gene coding sequence of (iii) further encodes at least one of the AAV Rep52 and/or AAV Rep40 polypeptide.

7. A cell comprising the circular nucleic acid of claim 1, wherein said cell does not comprise an AAV cap gene and is not able to express any AAV cap gene products, and further wherein said cell provides a conditional expression system for expressing said transgenic coding sequence.

8. The cell of claim 7, wherein said nucleic acid of claim 1 is comprised in a vector that does not comprise an AAV cap gene, and said cell is transfected with said vector.

9. A kit comprising the nucleic acid of claim 1, wherein said kit neither comprises the AAV cap gene nor means to express any AAV cap gene product.

10. The kit of claim 9, further comprising at least one of the following selected from:
at least one said helper polypeptide originating or derived from a virus selected from Adenoviridae and Herpesviridae, wherein said helper polypeptide is capable of activating at least one AAV promoter of the nucleic acid of claim 1,
at least one nucleic acid encoding at least one said helper polypeptide originating or derived from a virus selected from Adenoviridae and Herpesviridae, wherein said helper polypeptide is capable of activating at least one AAV promoter of the nucleic acid of claim 1,
at least one said helper polynucleotide originating or derived from a virus selected from Adenoviridae and Herpesviridae, wherein said helper nucleotide is capable of activating at least one AAV promoter of the nucleic acid of claim 1,
at least one cell capable of being transfected with the nucleic acid of claim 1,
at least one cell comprising the circular nucleic acid of claim 1, and
instructions for using the kit.

11. A method for conditional gene expression in a cell of claim 7, comprising inducing expression of the product encoded by said transgenic coding sequence of the nucleic acid of claim 1 after each said AAV promoter is activated by a said helper polypeptide or helper polynucleotide, wherein said method comprises at least one of the following:
providing to the cell of claim 7 at least one said helper polypeptide originating or derived from a virus selected from Adenoviridae and Herpesviridae, wherein said helper polypeptide is capable of activating at least one said AAV promoter of the nucleic acid of claim 1,
introducing into the cell of claim 7 at least one nucleic acid encoding at least one said helper polypeptide originating or derived from a virus selected from Adenoviridae and Herpesviridae, wherein said helper polypeptide is capable of activating at least one said AAV promoter of the nucleic acid of claim 1,
providing to the cell of claim 7 at least one said helper polynucleotide originating or derived from a virus selected from Adenoviridae and Herpesviridae, wherein said helper polynucleotide is capable of activating at least one said AAV promoter of the nucleic acid of claim 1, and
contacting the cell of claim 7 with at least one virus selected from Adenoviridae and Herpesviridae.

12. A method of determining whether a virus, said virus selected from Adenoviridae and Herpesviridae, is inhibited by an antiviral agent, said method comprising bringing into contact a cell of claim 7 with a sample comprising said virus wherein said contacting is effected (i) in the presence of said antiviral agent and (ii) in its absence, wherein a greater amount of product of the transgenic coding sequence of (v) in case (ii) is indicative of said virus being inhibited by said agent.

13. A method of detecting infectious virus in a sample, said virus selected from Adenoviridae and Herpesviridae, said method comprising bringing into contact a cell of claim 7 with a sample comprising or suspected of comprising said infectious virus, wherein the presence of product of the transgenic coding sequence of (v) is indicative of the presence of said infectious virus in said sample.

14. A method of quantifying infectious virus in a sample, said virus selected from Adenoviridae and Herpesviridae, said method comprising bringing into contact a cell of claim 7 with a sample comprising or suspected of comprising said infectious virus, wherein the amount of product of the transgenic coding sequence of (v) is indicative of the amount of said infectious virus in said sample.

15. A method for identifying a compound having antiviral activity against a virus, said virus selected from Adenoviridae and Herpesviridae, said method comprising the steps of:
(a) introducing into cells of a population of cells of claim 7, at least one nucleic acid encoding at least one helper polypeptide originating or derived from a virus selected from Adenoviridae and Herpesviridae;
(b) determining the amount of the product encoded by the transgenic coding sequence of (v) expressed by the cell population of step (a) after said introducing;
(c) contacting a population of cells of step (a) with the compound to be tested;
(d) determining the amount of the product encoded by said transgenic coding sequence of (v) expressed by the cell population of step (c) after said introducing; and
(e) comparing the amount of said product determined in step (b) with the amount of said product determined in step (d), wherein less product determined in step (d), relative to the product determined in step (b) indicates that the tested compound has antiviral activity.

16. The method of claim 15, further comprising providing in step (a) at least one helper polynucleotide originating or derived from a virus selected from Adenoviridae and Herpesviridae.

17. The method of claim 15, wherein said introducing comprises infection with a virus selected from Adenoviridae and Herpesviridae.

\* \* \* \* \*